United States Patent [19]

Haber et al.

[11] Patent Number: 5,282,806
[45] Date of Patent: Feb. 1, 1994

[54] ENDOSCOPIC SURGICAL INSTRUMENT HAVING A REMOVABLE, ROTATABLE, END EFFECTOR ASSEMBLY

[75] Inventors: Terry M. Haber, Lake Forest; William H. Smedley, Lake Elsinore; Clark B. Foster, Laguna Niguel, all of Calif.

[73] Assignee: Habley Medical Technology Corporation, Laguna Hills, Calif.

[21] Appl. No.: 933,468

[22] Filed: Aug. 21, 1992

[51] Int. Cl.$^5$ ............................................. A61B 17/00
[52] U.S. Cl. ........................................ 606/139; 606/144; 606/148; 606/205; 606/207; 606/208; 606/145; 606/146
[58] Field of Search .................... 606/1, 139, 142, 143, 606/147, 148, 205-209; 227/19, 175, 901

[56] References Cited

U.S. PATENT DOCUMENTS

| | | |
|---|---|---|
| 1,274,669 | 8/1918 | Bohn . |
| 2,363,334 | 11/1944 | Jones . |
| 3,168,097 | 2/1965 | Dormia . |
| 3,675,688 | 7/1972 | Bryan et al. ............ 606/143 |
| 3,895,636 | 7/1975 | Schmidt . |
| 3,949,924 | 4/1976 | Green .................... 227/19 |
| 4,152,920 | 5/1979 | Green . |
| 4,491,135 | 1/1985 | Klein . |
| 4,562,839 | 1/1986 | Blake, III et al. . |
| 4,580,567 | 4/1986 | Schweitzer et al. . |
| 4,643,190 | 2/1987 | Heimberger . |
| 4,674,501 | 6/1987 | Greenberg ............ 606/142 |
| 4,706,668 | 11/1987 | Backer . |
| 4,760,848 | 8/1988 | Hasson . |
| 4,815,476 | 3/1989 | Clossick . |
| 4,872,456 | 10/1989 | Hasson . |
| 4,890,615 | 1/1990 | Caspari et al. . |
| 4,898,157 | 2/1990 | Messroghli et al. . |
| 4,935,027 | 6/1990 | Yoon . |
| 4,944,093 | 7/1990 | Falk . |
| 4,950,273 | 8/1990 | Briggs . |
| 5,084,054 | 1/1992 | Bencini et al. . |
| 5,100,420 | 3/1992 | Green et al. ............ 227/19 |
| 5,147,373 | 9/1992 | Ferzli . |
| 5,176,702 | 1/1993 | Bales et al. ............ 606/205 |

FOREIGN PATENT DOCUMENTS

| | | |
|---|---|---|
| 0586661 | 3/1947 | United Kingdom . |
| 2044108 | 10/1980 | United Kingdom . |
| 2140735 | 12/1984 | United Kingdom ........ 606/205 |

OTHER PUBLICATIONS

JARIT Laparoscopic Cholecystectomy Instruments. STAR 2000 Series, 1991.

Primary Examiner—Stephen C. Pellegrino
Assistant Examiner—Jeffrey A. Schmidt
Attorney, Agent, or Firm—Townsend and Townsend Khourie and Crew

[57] ABSTRACT

An instrument (602), particularly suited for endoscopic use, has an elongate body, including a base (604) and an elongate spindle (630) rotatably mounted to the base. A removable end-effector assembly (612), mounted at the distal end of the spindle (630), includes end-effector elements (608, 610), such as a pair of jaws, actuated by finger and thumb rings (616, 618) mounted to the base. A rotary actuator trigger (78) is slidably mounted to the base. The spindle (630) has a spiral groove (632) engaged by a cam pin (82) extending from the trigger so that axial movement of the trigger causes rotary motion of the spindle and the end-effector assembly therewith. The spindle and end-effector assembly are sheathed by a nonrotating sleeve (688) with an unbroken outer surface. The sleeve can be releasably translated axially to release or engage an end-effector assembly, allowing use of alternate end-effector assemblies.

13 Claims, 29 Drawing Sheets

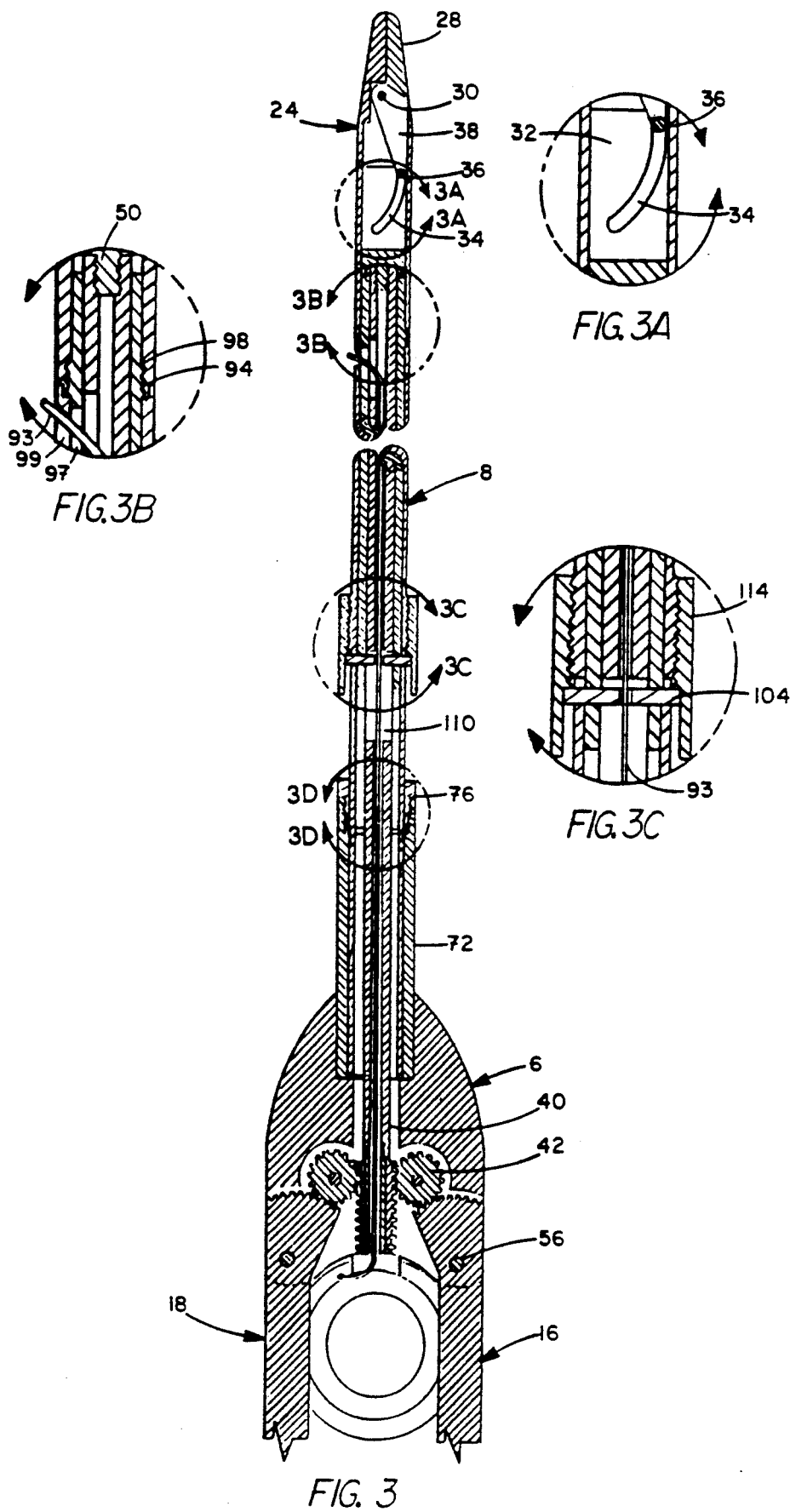

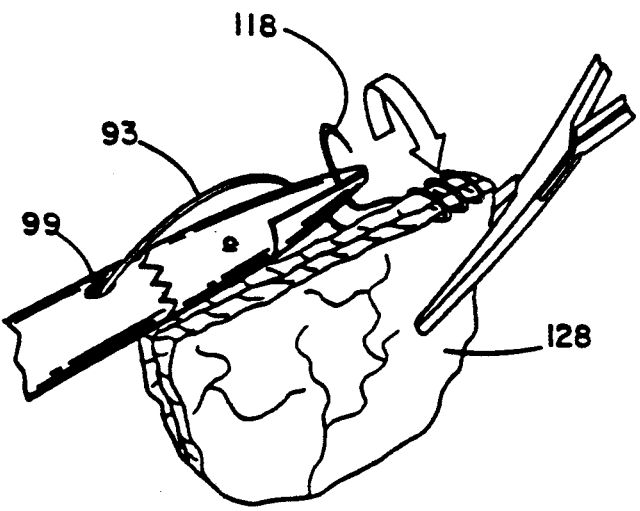
FIG. 6
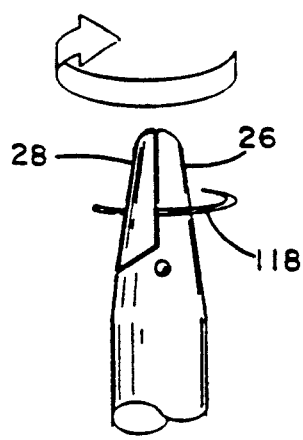 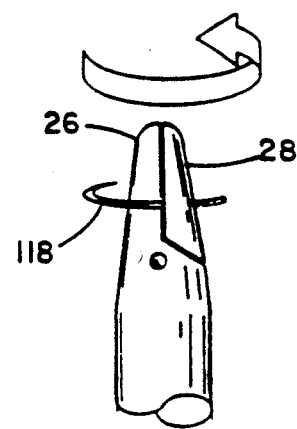
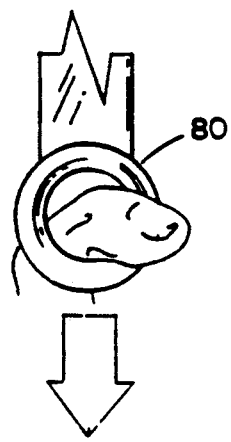 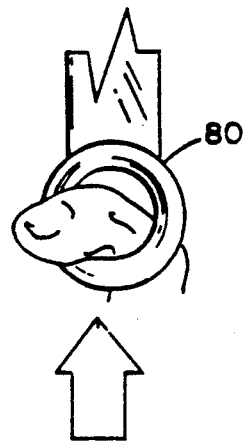
FIG. 6A                FIG. 6B

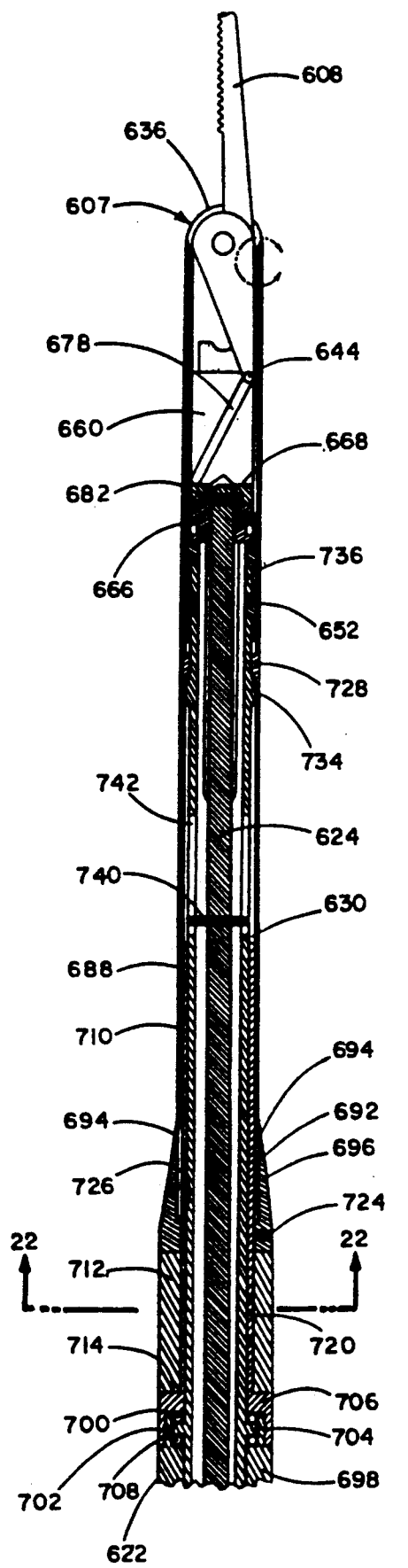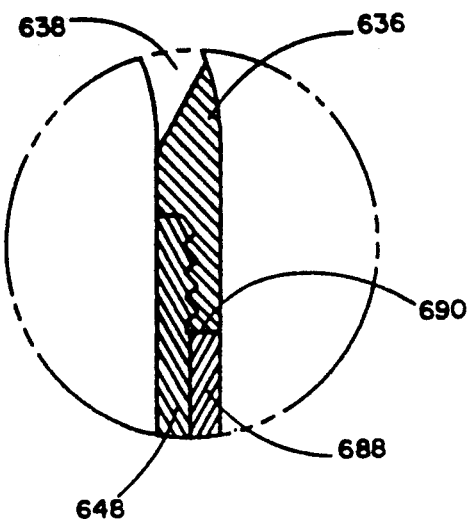
FIG. 17A
FIG. 17

ENDOSCOPIC SURGICAL INSTRUMENT HAVING A REMOVABLE, ROTATABLE, END EFFECTOR ASSEMBLY

CROSS REFERENCE TO RELATED APPLICATIONS

This is related to the following U.S. patent applications, the disclosures of which are incorporated by reference application No. 07/839,510, filed Feb. 21, 1992 for Needle Manipulator; application No. 07/850,674, filed Mar. 13, 1992 for Endoscopic Surgical Instrument; application No. 07/878,957, filed May 4, 1992 for Axially Extendable Endoscopic Surgical Instrument; and application No. 07/898,101, filed Jun. 12, 1992 for Improved Axially Extendable Endoscopic Surgical Instrument.

BACKGROUND OF THE INVENTION

The practice of endoscopic or minimally-invasive surgery is becoming more widely used because it is less traumatic than conventional open surgery, thus reducing hospitalization times and costs as well as minimizing patient risk and discomfort. With endoscopic surgery, only a relatively short incision is necessary, with the endoscopic instrument being passed through this incision. A tissue-protective port is sometimes used to minimize tissue trauma on the walls of the incision. Various types of endoscopic instruments are passed through the small incision and appropriate surgical procedures are carried out.

One type of endoscopic instrument is forceps having end-effectors specially configured to grasp, manipulate or cut or staple tissue. Conventional forceps typically use scissors-type of thumb and finger rings. Such forceps, although appropriate for cutting and simple grasping tasks for open surgical procedures, are unusable for many minimally-invasive surgical tasks, such as placing sutures or staples during endoscopic procedures; conventional forceps require the physician to radially reposition the entire instrument to adjust the radial orientation of the end-effector.

SUMMARY OF THE INVENTION

The present invention is directed to a minimally-invasive surgical instrument which permits the physician to insert the instrument into and withdraw it from small incisions or lumen in or of the tissue without tearing or traumatizing the tissue and without generating frictional forces between the shaft of the instrument and the proximal and distal aspects of a tissue-protective endoscopic access port, which may tightly engage the instrument, and instrument parts which move during manipulation of the instrument. The instrument of the present invention further facilitates the ease with which the operative end-effector of the instrument can be attached to or released from the instrument, quickly and easily even under conditions prevailing in the operating room, for the replacement of the end-effector assembly as well as for resterilization of the instrument after use.

Briefly, the surgical instrument of the present invention has a base at the proximal end of the instrument, a stationary, tubular housing projecting from the base, and an end-effector assembly projecting from an open end of the housing and defining the distal end of the instrument. The end-effector assembly includes at least one and typically a pair of opposing, movable end-effector elements, such as jaws, dilators or clamps, which can be opened and closed as well as rotated about the axis of the housing into a desired position. An end-effector element opening mechanism is operable from the base, typically via finger and thumb rings which can be pivoted between open and closed positions in a scissors-like fashion. Their pivotal movement is translated into axial movement of a drive rod disposed at the center of the housing and having a distal end which is releasably lockable to the end-effector assembly. A rotating mechanism, preferably actuated with a reciprocable trigger ring at the base, includes a rotatable, tubular spindle that surrounds the drive rod and is releasably locked to the end-effector assembly, preferably with a pair of opposing spring arms on the spindle which can be biased radially inward into a releasing position proximal end of the tubular housing and pulling it axially rearwardly towards the base.

The exterior of the housing is smooth and continuous so that it easily slides axially or rotates radially within a tightly engaging incision, tissue lumen, or tissue-protective endoscopic port to facilitate the insertion and withdrawal of the instrument. During use, the stationary housing prevents any contact between the surrounding endoscopic port and the movable rod and spindle, both of which are located on the inside of the housing, to minimize friction and enhance the smoothness and preciseness with which the instrument can be manipulated.

Other features and advantages of the invention will be evident from the following description in which the preferred embodiments have been set forth in detail in conjunction with the accompanying drawings.

BRIEF DESCRIPTION OF THE DRAWINGS

FIG. 3 is a cross-sectional view of a portion of the needle manipulator of FIG. 1 with the end-effector elements in a closed position;

FIGS. 3A-3D show portions of the needle manipulator of FIG. 3 enlarged to show detail;

FIG. 6 is an enlarged view of the end-effector assembly of FIG. 1 shown manipulating a needle to suture tissue:

FIGS. 6A and 6B illustrate the rotary movement of the end-effector assembly and needle of FIG. 6 as the trigger is pulled and pushed, respectively, through the patient's tissue;

FIG. 17 is a cross-sectional view of that portion of the instrument of FIG. 16 which connects to the base of the instrument shown in the lower third of FIG. 16;

FIG. 17A is an enlarged detail and is taken on line A—A of FIG. 17;

DESCRIPTION OF THE PREFERRED EMBODIMENTS

Figure 1:
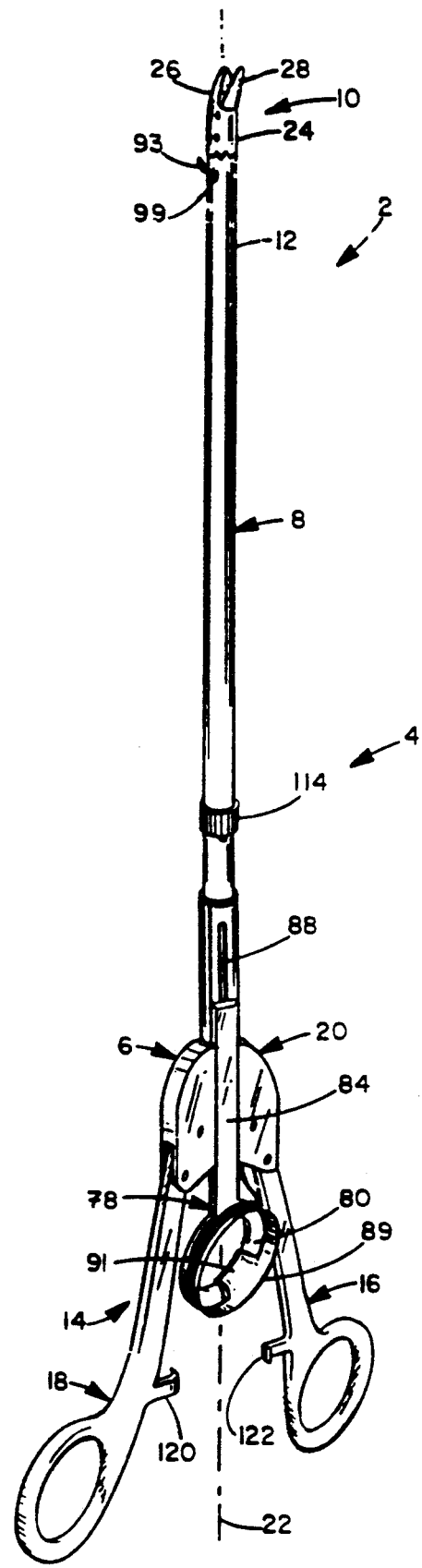
FIG. 1 is an overall perspective view of a needle manipulator type of endoscopic surgical instrument.

FIG. 1 illustrates a rotational end-effector needle manipulator type of endoscopic surgical instrument. Needle manipulator 2 includes an elongate body 4, the body including a base 6 and an elongate end-effector carrier tube 8. Manipulator 2 also includes an end-effector assembly 10 mounted to the distal end 12 of tube 8 and an end-effector element driver assembly 14. End-effector element driver assembly 14 is used to manipulate the end-effector elements carried by the end-effector assembly as is described below through the opening and closing of end-effector element actuating finger and thumb rings 16, 18. Manipulator 2 further includes an end-effector element rotator assembly 20 used to rotate end-effector carrier tube 8 and end-effector assembly 10 therewith about the longitudinal axis 22 of the manipulator.

Figure 2:
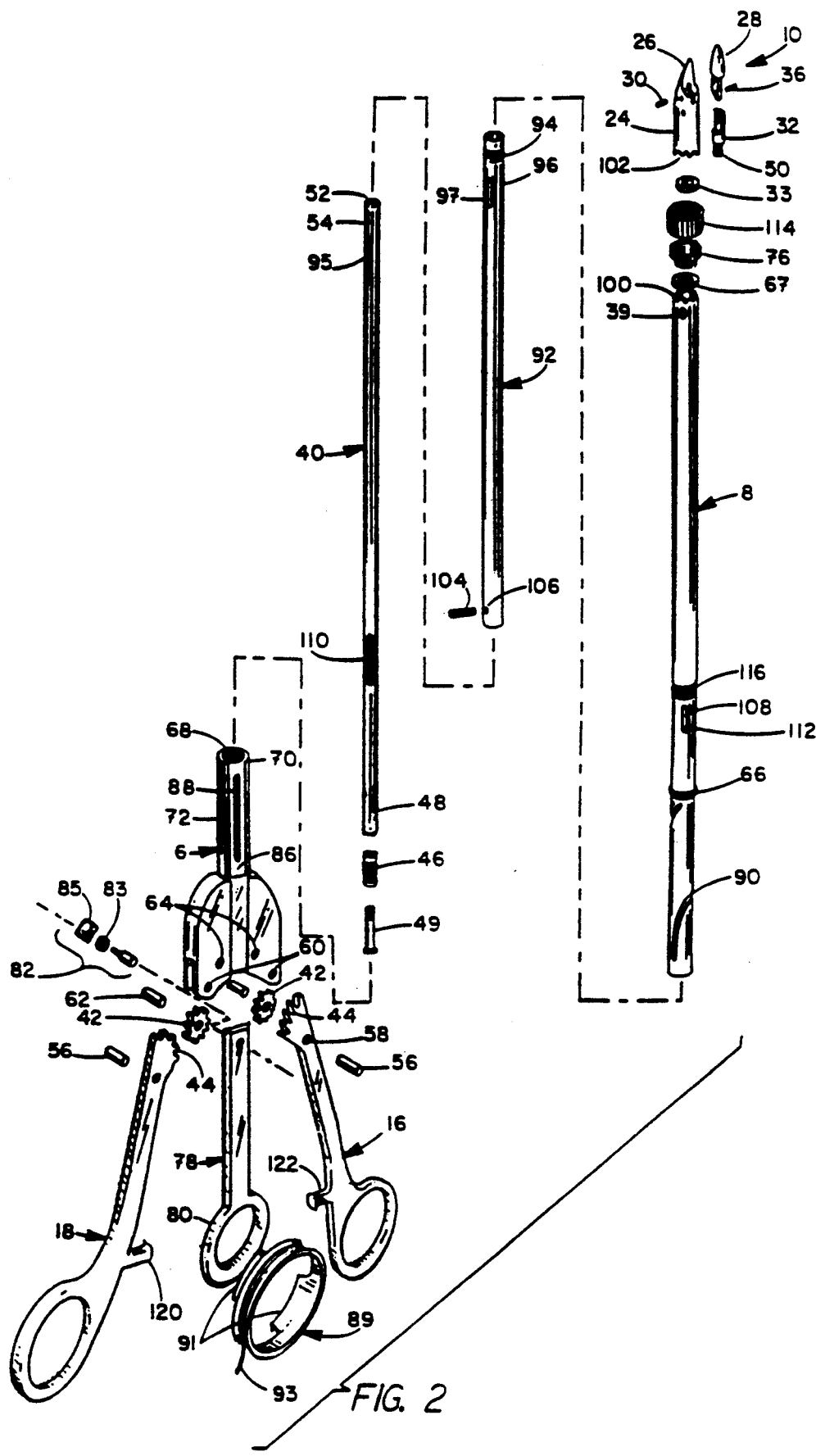
FIG. 2 is an exploded isometric view of the needle manipulator of FIG. 1.
Figure 3D:
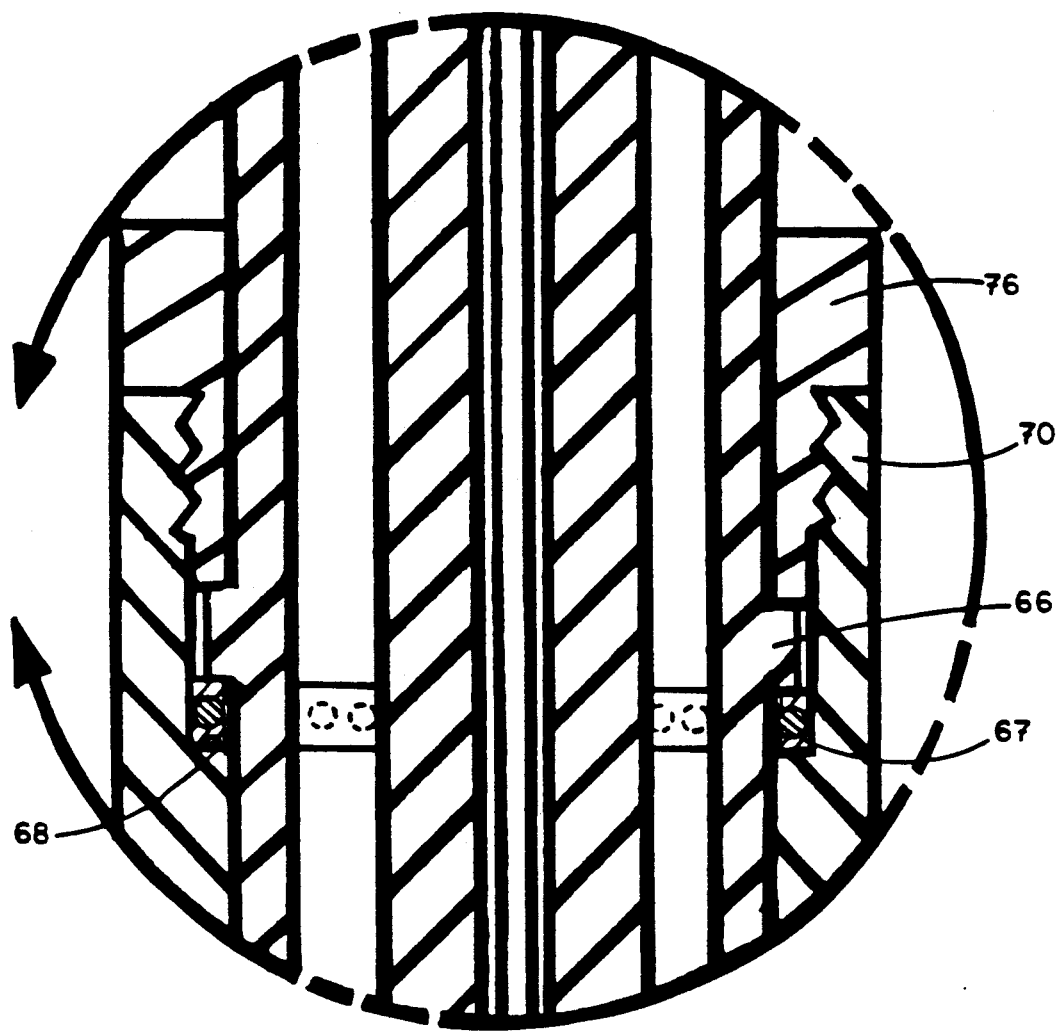
Figure 4:
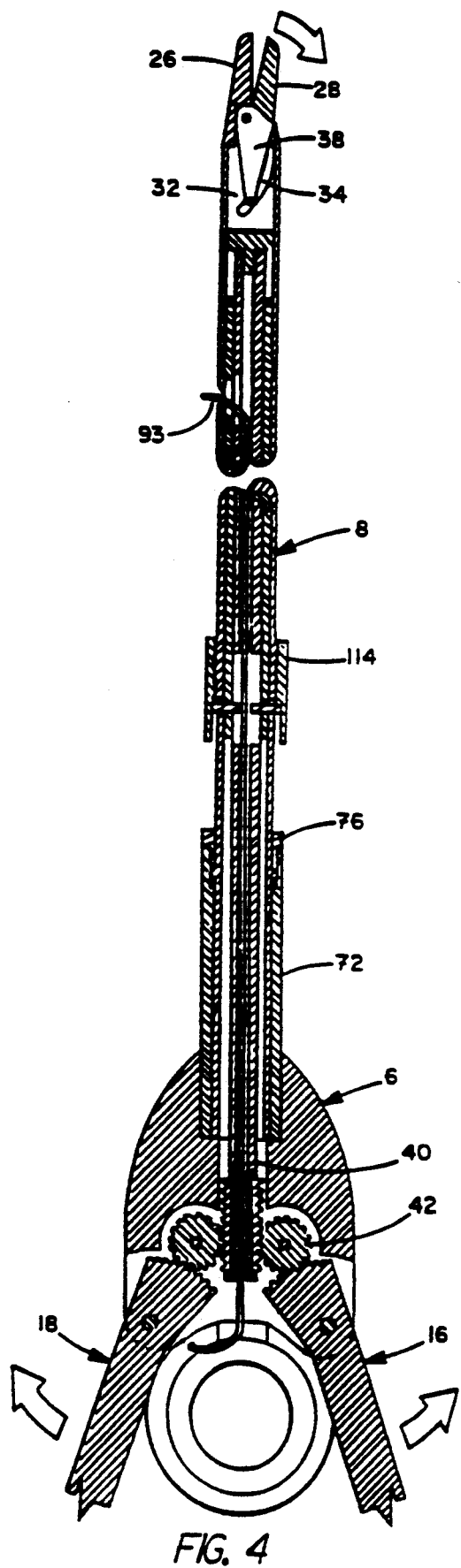
FIG. 4 shows the needle manipulator of FIG. 3 with the end-effector elements in the open position.
Figure 5:
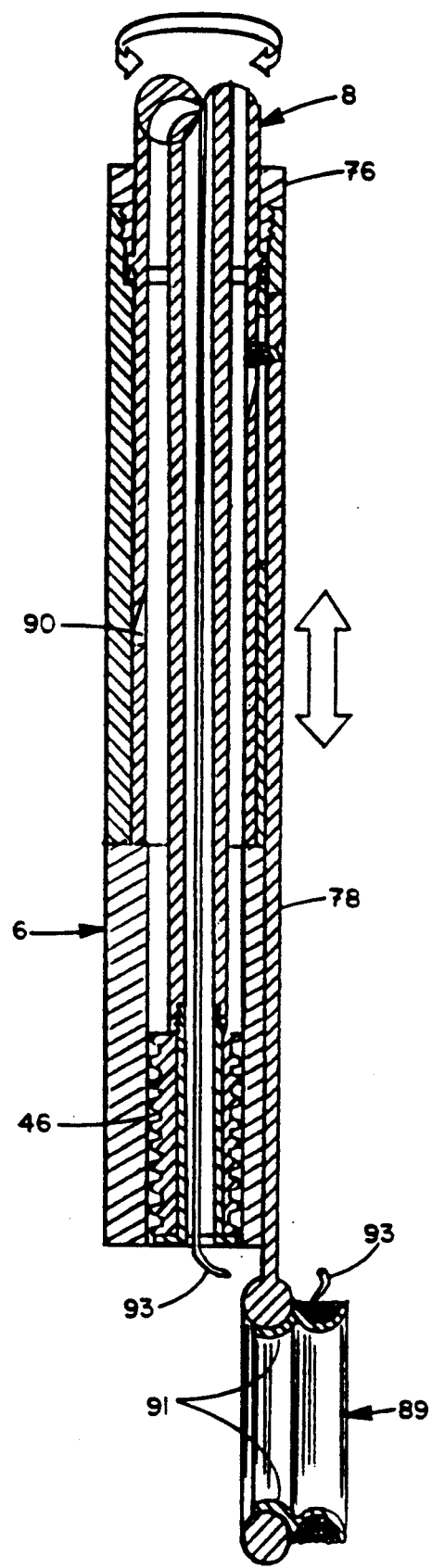
FIG. 5 is a cross-sectional view of a portion of the needle manipulator of FIG. 1 taken in a plane perpendicular to the plane of FIG. 3.
Figure 7:
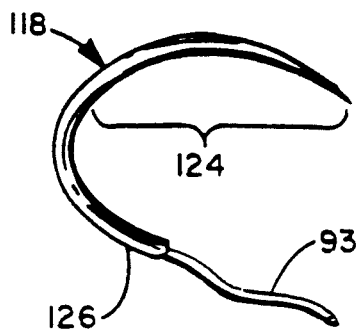
FIGS. 7 and 7A are enlarged plan and side views of the needle of FIG. 6 showing the attachment of the suture material and the special shape of the needle.
Figure 7A:
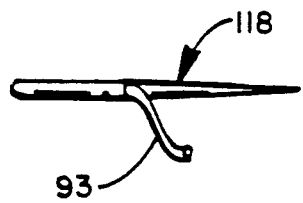
Figure 7B:
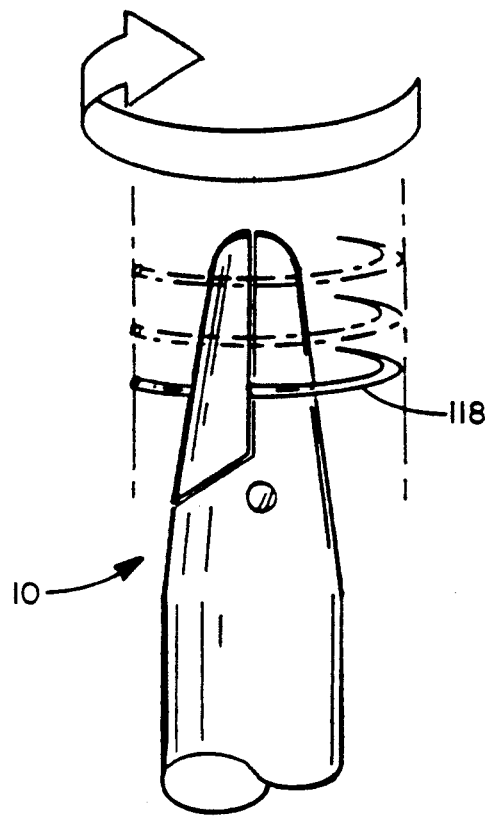
FIG. 7B illustrates the progression of the needle of FIG. 6 after successive stitches caused by rotation of the end-effector assembly and needle.
Figure 8A:
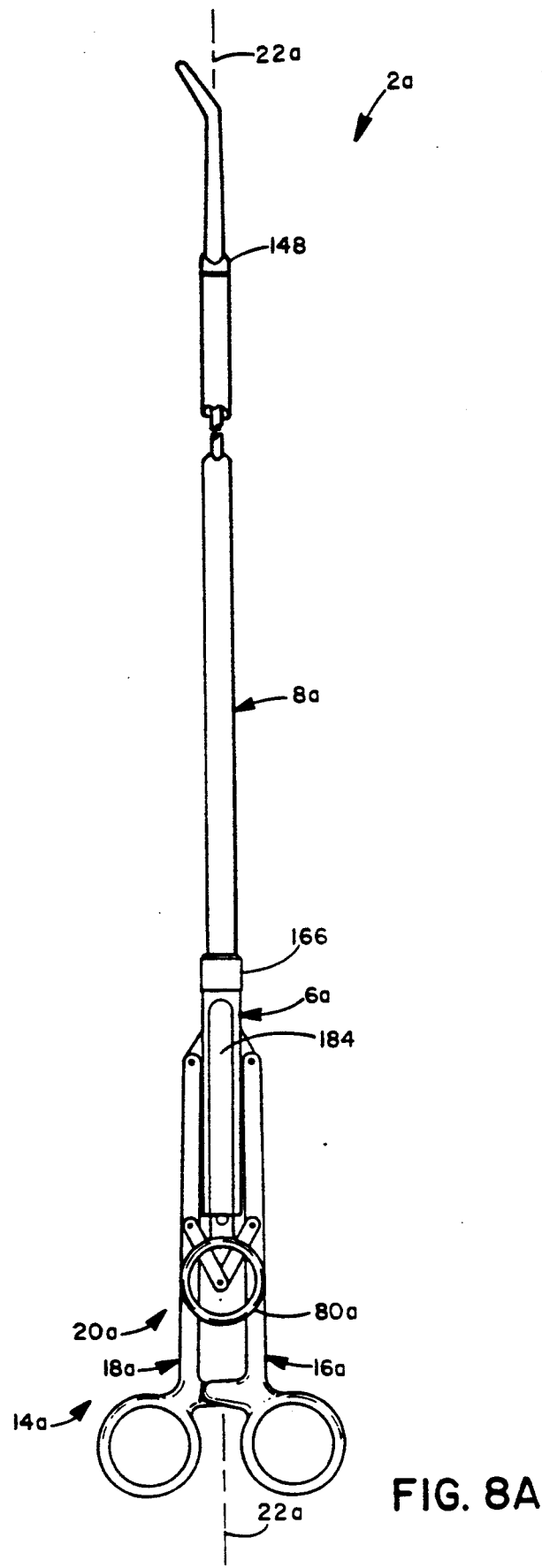
FIGS. 8A, 8B and 8C are side views of a grasping type of endoscopic surgical instrument made according to the invention shown in a closed end-effector element position in FIG. 8A, an open end-effector element position in FIG. 8B with the end-effector assembly rotated 90° from the position of FIG. 8A, and a closed end-effector element position in FIG. 8C with the end-effector assembly rotated 180° from the position of FIG. 8A.
Figure 8B:
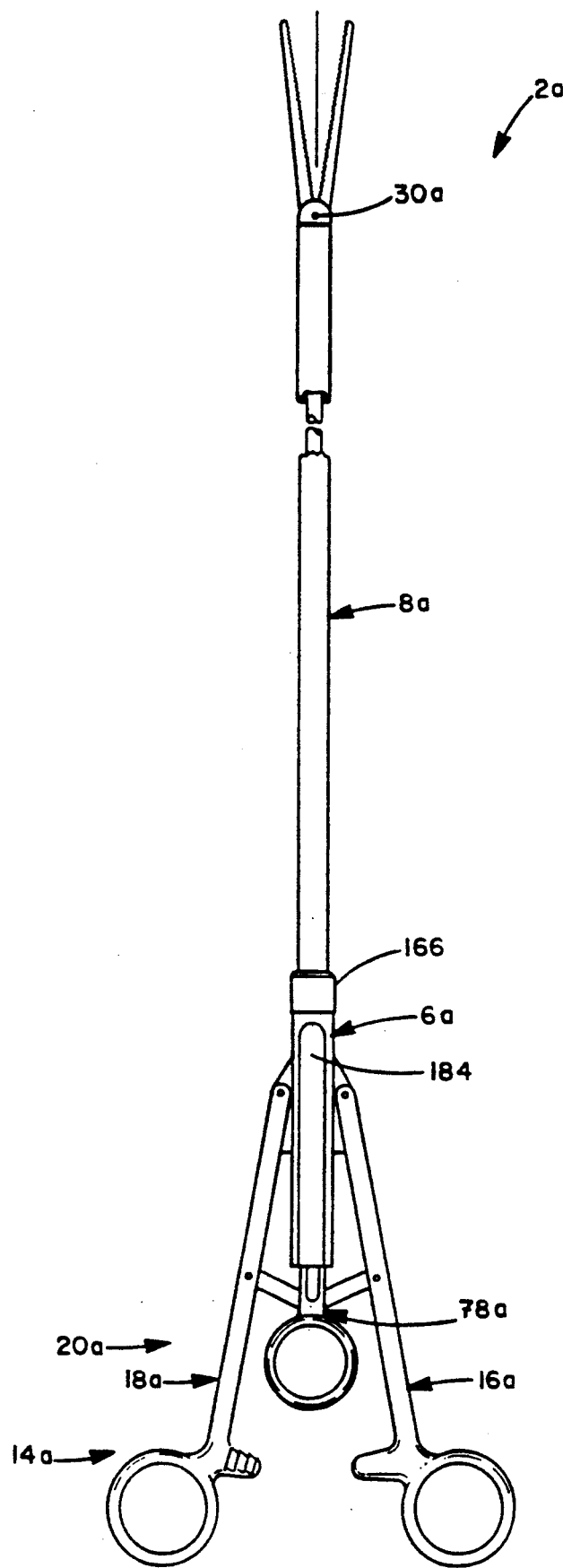
Figure 8C:
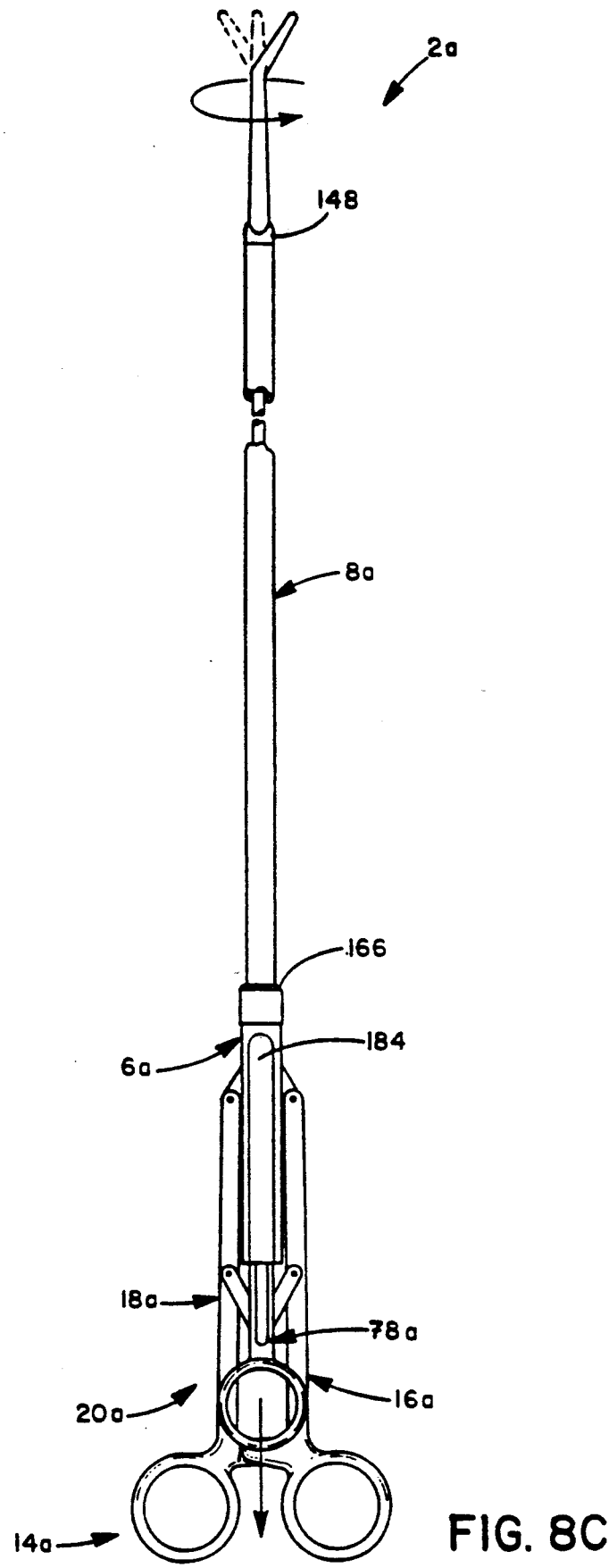

FIG. 2 illustrates end-effector assembly 10 as including an end-effector 24 having a fixed end-effector element 26 integral with end-effector 24 and a movable end-effector element 28 secured to end-effector 24 by a pivot pin 30. End-effector assembly 10 also includes an adapter 32 sized to fit within and slide within the hollow interior of end-effector assembly 10. Adapter is held within the interior of end-effector 24 by a ring 33 press fit into the end-effector interior. Adapter 32 has a cam slot 34 within which a drive pin 36 extending from an end 38 of movable end-effector element 28 rides. Thus, axial movement; that is, movement parallel to axis 22, of adapter 32 causes movable end-effector element 28 to move from the closed end-effector element position of FIG. 3 to the open end-effector element position of FIG. 4. This is accomplished by the manipulation of end-effector element driver assembly 14. (See FIG. 1.)

End-effector element driver assembly 14 includes finger and thumb rings 16, 18 coupled to an axial drive rod 40 through the engagement of idler gears 42 with drive gear segments 44 formed on finger and thumb rings 16, 18 and a rotary rack 46 formed on the proximal end of 48 of drive rod 40. Rack 46 is secured to end 48 by a screw 49 to permit rack 46 to rotate freely. Adapter 32 includes a threaded end-effector 50 which engages a threaded hole 52 at the distal end of 54 of rod 40. Finger and thumb rings 16, 18 are pivotally mounted to base 6 through the use of pivot pins 56 passing through pivot holes 58 formed in rings 16, 18 and pivot pin bores 60 formed in base 6. Idler gears 42 are secured to base 6 by idler gear pins 62 which pass through bores in the idler gears and through idler gear pin holes 64 in base 6.

End-effector carrier tube 8 has an annular shoulder 66 sized and positioned to seat against a thrust bearing 67 supported by an internal annular surface 68 formed at the distal end 70 of barrel portion 72 of base 6. See FIG. 3D. The proximal end 74 of tube 8 is maintained within base 6 by an externally threaded ring 76. Ring 76 is sized so that when the ring is secured against distal end 70 of barrel portion 72, tube 8 is securely mounted to base 6 but is free to rotate within the base. Thrust bearing 67 helps to ensure the free rotation of tube 8 during use.

End-effector element rotator assembly 20 includes a rotary actuator trigger 78 having a finger ring 80 at its proximal end and a cam pin 82 at its distal end. Trigger 78 incudes elongate portion 84 having a dovetail or trapezoidal cross-sectional shape which slides within a similarly configured dovetail slot 86 formed along the length of base 6. Pin 82 passes through an axial slot 88 formed in barrel portion 72 along slot 86. Pin 82 passes through slot 88 to engage a spiral groove 90 formed in proximal end 74 of tube 8. Pin 82 includes a ring 83 which rides within slot 88 and a guide 85 which rides within spiral groove 90, both ring 83 and guide 85 preferably made of PTFE. Thus, axial movement of trigger 78 causes pin 82 to ride along spiral groove 90, thus rotating tube 8 and end-effector assembly 10 therewith about axis 22.

End-effector assembly 10 is secured to end-effector carrier tube 8 using a hollow end-effector mounting tube 92. End-effector mounting tube 92 has external threads 94 at its distal end 96 which engage internal threads 98 formed within the interior of end-effector 24. End-effector 24 and end-effector carrier tube 8 have opposed, complementary tooth surfaces 100, 102 which, when engaged, keep end-effector assembly 10 from rotating relative to end-effector carrier tube 8. Tube 8, mounting tube 92, and drive rod 40 are secured to one another by a common pin 104. Pin 104 passes through a bore 106 in mounting tube 92, a short slot 108 in carrier tube 8, and a long slot 110 in drive rod 40. Common pin 104 is maintained at the proximal end 112 of slot 108, thus keeping tooth surfaces 102, 100 engaged, through the use of an internally threaded ring 114 threaded onto external threads 116 formed on the outside of tube 8 adjacent slot 108. Slot 110, being longer than slot 108, can still move axially through the manipulation of finger and thumb rings 16, 18, thus causing end-effector elements 26, 28 to open and close.

A suture material supply spool 89 is mounted to finger ring 80 through the use of snap flanges 91 which engage the inside of the finger ring. Suture material 93 is directed from needle 118, through hole 99 in tube 8, through slots 95, 97 in rod 40 and tube 92, through the center of rod 40, and is wound about spool 89.

The operation of needle manipulator 2 will now be described. The user places his or her thumb and middle finger through thumb and finger rings 18, 16. Rings 18, 16 are separated, as suggested in FIG. 4, causing drive gear segments 44 to rotate idler gears 42 which, in turn, drive rotary rack 46 axially; that is, parallel to axis 22. This causes adapter 32 to move axially so that drive pin 36 moves along cam slot 34, thus opening end-effector elements 26, 28 through the pivotal movement of movable end-effector element 28. A needle 118 is placed between end-effector elements 26, 28 and is secured in place by moving finger rings 16, 18 back towards one another to the position of FIGS. 1 and 3. Needle 118 is locked between end-effector elements 26, 28 through the engagement of catches 120, 122 carried by rings 16, 18. The manipulation of rotary actuator trigger 78 parallel to axis 22 causes pin 82 to ride along spiral groove 90, thus rotating end-effector carrier tube 8 and end-effector assembly 10 therewith about axis 22. End-effector mounting tube 92 and axial drive rod 40 are likewise rotated about axis 22 upon the actuation of trigger 78 due to the interlocking engagement of common pin 104 with all three members. With needle manipulator 2, the user's hand, wrist and arm can be generally aligned with axis 22 for enhanced control.

The reciprocal movement of trigger 78 causes end-effector assembly 10 and needle 93 to move in opposite rotary directions. See FIGS. 6, 6A and 6B. In the preferred embodiment this movement is through an arc of about 240°. Only when needle 93 is moved in the appropriate rotary direction, clockwise in FIG. 6, will the needle pierce tissue 128. After the piercing movement, the user releases needle 118 from between end-effector elements 26, 28, rotates end-effector assembly 10 in the opposite direction, regrasps needle 118 between end-effector elements 26, 28, pulls needle 118 completely through tissue 128, repositions needle 118 between end-effector elements 26, 28 at a position 126 along the needle, and repeats the process.

Needle 118 has a generally elliptical shape with a main portion 124 having a generally circular shape. Needle 118 can be grasped between end-effector elements 26, 28 at a position 126 adjacent the attachment point for suture material. Point 126 is located at about the center of the generally circular arc formed by a main portion 124 so that when end-effector assembly 10 is rotated about axis 22, main portion 124 moves along a generally circular path. This minimizes trauma to tissue 128 and makes the procedure easier to perform.

Turning now to FIGS. 8–10B, an alternative embodiment of the endoscopic medical instrument of FIGS. 1–7B is shown. Parts of the alternative embodiment which correspond to the embodiment of FIG. 1 have like reference numerals. The alternative embodiment is an endoscopic medical instrument of the grasping type having a pair of movable end-effector elements 28a, 28b as part of the end-effector assembly 10a. Instrument 2a includes broadly an elongate body 4a, an end-effector assembly 10a removably mounted to the distal end 12a of an end-effector carrier tube 8a, a driver assembly 14a, which causes end-effector elements 28a, 28b to move between their open and closed positions, and an end-effector element rotator assembly 20a, which causes end-effector assembly 10a, and end-effector elements 28a, 28b therewith, to rotate about axis 22a.

End-effector elements 28a, 28b include outer portions 140 and arm portions 142 connected by hubs 144 having holes 146 formed therein. End-effector assembly 10a also includes a circular, hollow end-effector coupler plug 148 having a through hole 150 formed perpendicular to axis 22a. End-effector elements 28a, 28b are mounted within end-effector coupler plug 148 and are pivotally secured within the plug by pivot pin 30a. The interior of end-effector coupler plug 148 is sized to permit end-effector elements 28a, 28b to move between their open and closed positions of FIGS. 8A and 8B.

Figure 10A:
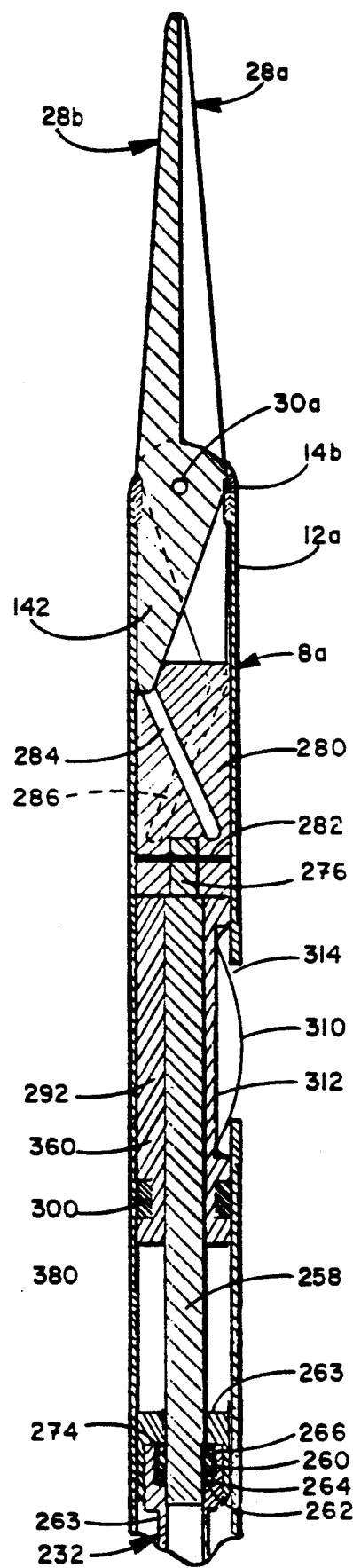
FIGS. 10A and 10B are longitudinal cross-sectional views of the distal and proximal portions of the instrument of FIGS. 9A and 9B.
Figure 10B:
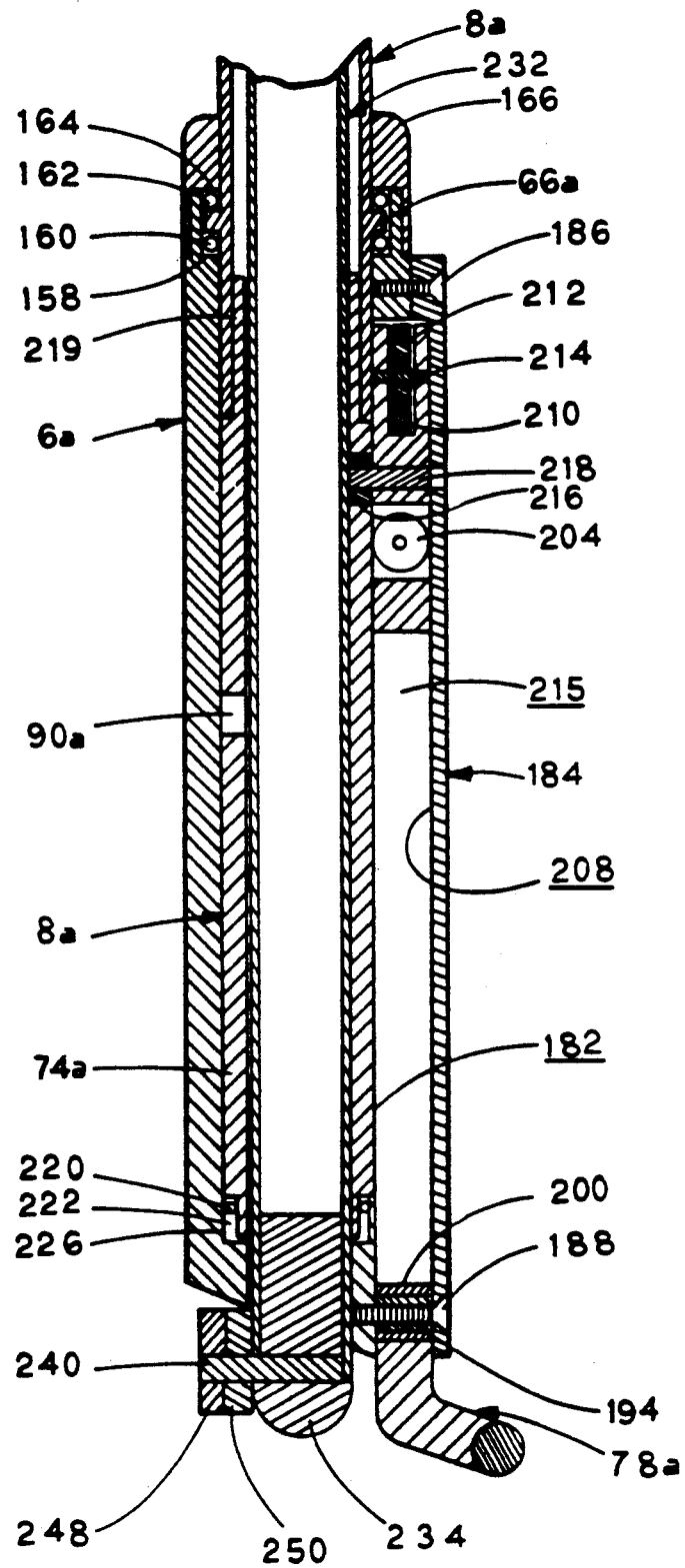

End-effector coupler plug 148 has external threads 152 formed on one end. Threads 152 are sized to engage internal threads 154 formed at distal end 12a of end-effector carrier tube 8a. In this way, end-effector assembly 10a can be removably secured to body 4a of instrument 2a. End-effector carrier tube 8a is sized so that proximal end 74a fits within the hollow interior 156 of base 6a. Base 6a, as shown in FIG. 10B, has an inner shoulder 158 which supports annular shoulder 66a of end-effector carrier tube 8a. A set of ball bearings 160 is positioned between shoulder 66a and shoulder 158. Another set of ball bearings 162 is situated between annular shoulder 66a and an inner shoulder 164 of an end-effector carrier tube retaining nut 166. Nut 166 has a threaded interior 168 which engages the threaded exterior 170 of base 6a. Shoulders 158, 164 are positioned so that end-effector carrier tube 8a is secured axially to base 6a but is allowed relatively free rotary movement with respect to the base by virtue of ball bearing sets 160, 162.

Finger and thumb rings 16a, 18a are pivotally mounted to lugs 172 of base 6a using pins 174 which pass through openings 176 formed in the clevis ends 178 of rings 16a, 18a and corresponding holes 180 formed in lugs 172. Manipulation of rings 16a, 18a is used to open and close end-effector elements 28a, 28b and will be discussed below.

Base 8a has flat face 182 extending substantially along its entire length. A hollowed-out cover 184 is secured to base 6a by a pair of screws 186, 188. Screw 186 threads into a hole 190 in base 6a adjacent the distal end of flat face 182. Screw 188 passes through the hollow interior 192 of a standoff 194 and engages a threaded hole 196 formed in flat face 182 at the proximal end of axial slot 88a. A roller 200 is sized to be mounted over and rotate freely about standoff 194. Roller 200 is sized to fit within a slot 202 formed in trigger 78a and helps to stabilize trigger 78a as the trigger moves parallel to axis 22a. The stability of trigger 78a is also aided by the use of a pair of rollers 204 on either side of trigger 78a at the distal end 206 of the trigger. Rollers 204 ride between surface 182 and the overlying surface 208 defined by cover 184 on the side thereof opposite flat face 182. Side-to-side movement of distal end 206 of trigger 78a is restricted by engagement of a roller 210 mounted in a slot 212 at distal end 206 of trigger 78a by a pin 214. Roller 210 is sized to ride along the side surfaces 215 of the hollow interior of cover 184.

Trigger 78a also includes a cam pin 82a. Cam pin 82a includes a cam roller 216 secured to distal end 206 by a pin 218. Cam pin 82a is positioned to extend through axial slot 88a and engage spiral groove 90a at proximal end 74a of end-effector carrier tube 8a. Thus, axial movement of trigger 78a causes cam pin 82a to move along spiral groove 90a, thus rotating end-effector carrier tube 8a and end-effector assembly 10a therewith about axis 22a.

FIG. 10B shows that proximal end 74a is thicker than the remainder of base 8a. This is to provide a deeper spiral groove 90a and thus a better camming surface for cam roller 216 to ride against. This dual wall thickness is achieved by overlapping tubes having different wall thicknesses as shown at overlapping region 219.

Lateral support of proximal end 74a within base 6a is aided by the use of a set of ball bearings 220 housed within an annular cavity 222. Cavity 222 is defined between the end-effector 224 of end 74a and a cupped shaped region 226 formed within base 6a adjacent proximal end 198.

Figure 9A:
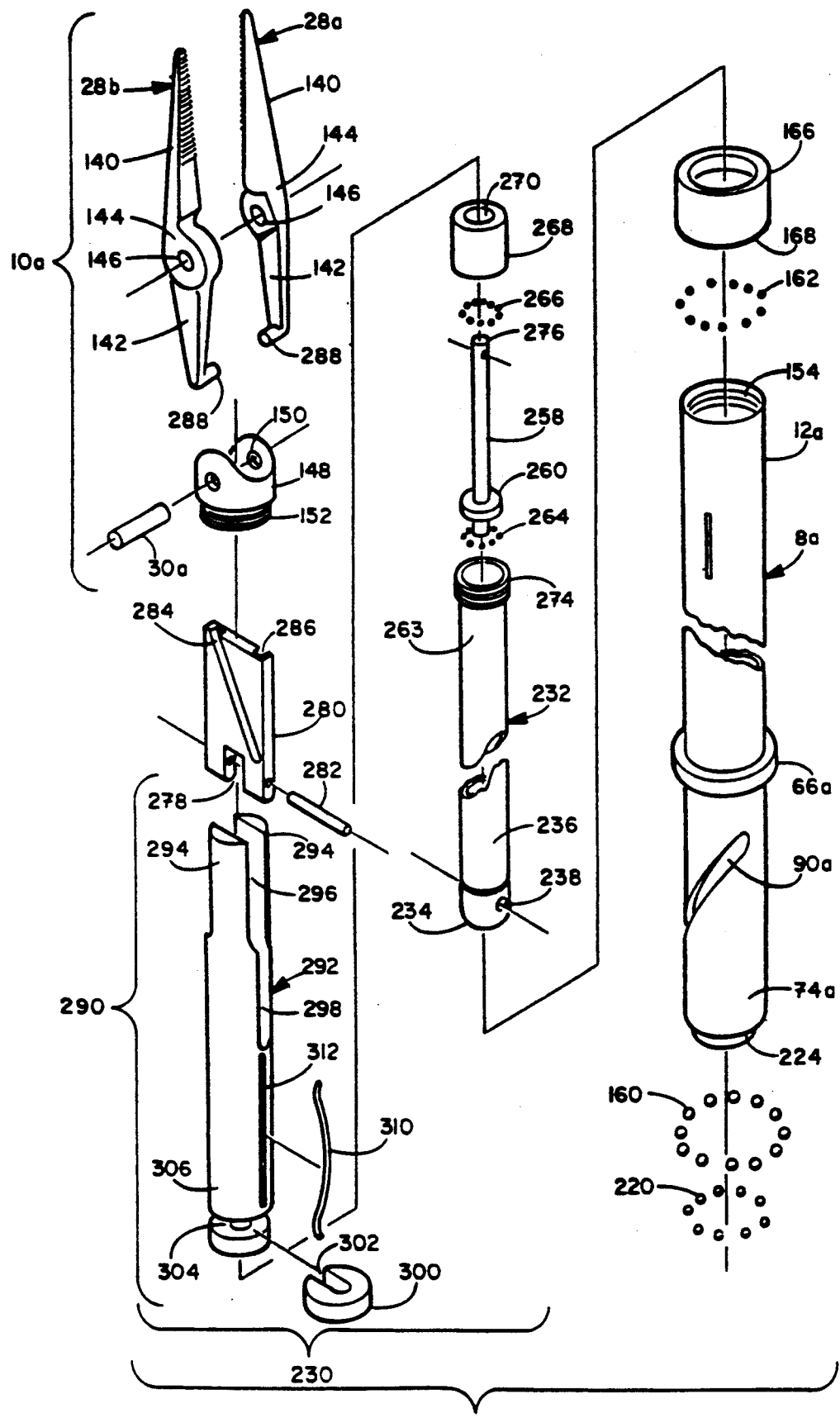
FIGS. 9A and 9B are exploded isometric views of the distal and proximal portions of the instrument of FIG. 8 shown with straight rather than offset end-effector.

The remainder of end-effector element driver assembly 14a, in addition to finger and thumb rings 16a, 18a, will now be discussed. As shown in FIG. 9A, an axial drive tube assembly 230 includes an axial drive tube 232 having a plug 234 at a proximal end 236. Plug 234 has a transverse bore 238 through which a common pin 240 passes. Pin 240 also passes through aligned bores 242 formed in the overlapping ends 244, 246 of links 248, 250. Links 248, 250 are pivotally connected to finger and thumb rings 16a, 18a by pins 252 passing through holes 254, 256 formed in links 248, 250 and rings 16a, 18a. Thus, movement of finger and thumb rings 16a, 18a towards and away from each other causes links 248, 250 to articulate, thus driving axial drive tube 232 along axis 22a.

Axial drive tube assembly 230 also includes a flanged draw bar 258 with a flange 260 at a proximal end thereof. Flange 260 is sized to lie adjacent an internal shoulder 262 formed at the distal end 263 of tube 232 with a set of ball bearings 264 captured therebetween. A second set of ball bearings 266 is positioned on the other side of flange 260. A draw bar retaining nut 268 has a central bore 270 sized to fit over flanged draw bar 258. Nut 268 has an internal shoulder 272 which rests against the lip 274 of tube 232 to capture ball bearings 266 between nut 268, bar 258 and tube 232. Flanged draw bar 258 is thus fixed axially to axial drive tube 232 but is allowed to freely rotate within the axial drive tube.

The distal end 276 of bar 258 fits within a cut-out region 278 formed in a flattened rectangular cam block 280. Cam block 280 is secured to distal end 276 by a pin 282 passing through both. Cam block 280 has a pair of slots 284, 286 formed on either side of cam block 280 and angled in opposite directions. Arms 142 of end-effector elements 28a, 28b each have inwardly extending pins 288 sized to engage slots 284, 286. Thus, axial movement of axial drive tube 232, which also moves flanged draw bar 258 and cam block 280 therewith, causes cam block 280 to move parallel to axis 22a, thus causing pins 288 to slide along slots 284, 286; this causes end-effector elements 28a, 28b to open and close in a grasping action.

Axial drive tube assembly 230 also includes a fork assembly 290 for stabilizing cam block 280 during use. Fork assembly 290 includes a fork 292 having a pair of arms 294 defining wider and narrower gaps 296, 298 therebetween. Wider gap 296 is sized to encompass arms 142 of movable end-effector elements 28a, 28b, while narrower gap 298 is sized to lie along either side and guide cam block 280.

Fork assembly 290 also includes a U-collar 300 having a slot 302 formed therein. Slot 302 is sized to fit loosely within an annular groove 304 formed at the proximal end 306 of fork 292. The outer circumference of U-collar 300 is sized to create a relatively tight friction fit within the interior 308 of end-effector carrier tube 8a. Thus, fork assembly 290 is fixed axially within end-effector carrier tube 8a while flanged draw bar 258 moves axially with fork 292.

Fork assembly 290 also includes a spring 310 partially housed within a fork spring slot 312 formed in fork 292 between groove 304 and narrower gap 298. Spring 310 is sized and positioned to engage a tube spring slot 314 formed in end-effector carrier tube 8a. In this way, fork assembly 290 is kept from rotating axially within end-effector carrier tube 8a. However, when first mounting end-effector assembly 10a to distal end 12a of end-effector carrier tube 8a, the user can depress spring 310 and allow fork assembly 290 to rotate along with cam block 280, end-effector assembly 10a and flange draw bar 258 until end-effector coupler plug 148 is screwed fully onto threads 154 of end-effector carrier tube 8a. At this point, spring 310 is allowed to freely enter slot 314 to prevent fork assembly 292 from rotating within end-effector carrier tube 8a. Thus, fork assembly 290 is used for two primary purposes: to guide and stabilize cam block 280 and arms 242 of end-effector elements 28a, 28b and to keep end-effector assembly 10a from unscrewing from end-effector carrier tube 8a.

In use, assuming end-effector assembly 10a must be changed, spring 310 is depressed through slot 314, and end-effector assembly 10a is unscrewed from internal threads 154 at distal end 12a of end-effector carrier tube 8a. An appropriate end-effector assembly is then threaded onto distal end 12a. Using end-effector assembly 10a, pins 288 are guided into slots 284, 286 to permit both end-effector elements 28a, 28b to move. In appropriate cases, a different cam block 280 could be used to accommodate a different type of motion; also, the end-effector assembly could be constructed so that only one end-effector element moves. End-effector assembly 10a is rotated about axis 22a by the manipulation of trigger 78a. The axial movement of trigger 78a causes end-effector carrier tube 8a and end-effector assembly 10a secured thereto to rotate about axis 22a. Once properly oriented, the user opens and shuts end-effector elements 28a, 28b by opening and closing finger and thumb rings 16a, 18a. Doing so articulates links 248, 250 which are coupled to axial drive tube 232 through common pin 240 and plug 234. Axial movement of drive tube 232 causes like axial movement of drawbar 258 which, being pinned to cam block 280 by pin 282, moves the cam block axially along axis 22a. The axial movement of cam block 280 causes transverse pivotal movement of end-effector elements 28a, 28b as pins 288 ride along slots 284, 286 to provide the desired grasping action.

The invention has been shown in two different embodiments, one specially adapted as an endoscopic needle manipulator while the other as an endoscopic tissue grasper or manipulator. The invention can also be practiced using end-effectors and end-effector assemblies configured for other uses. For example, end-effector assemblies adapted for dilating a region, cutting tissue, stapling tissue or knotting suture material could be used as well.

Figure 11:
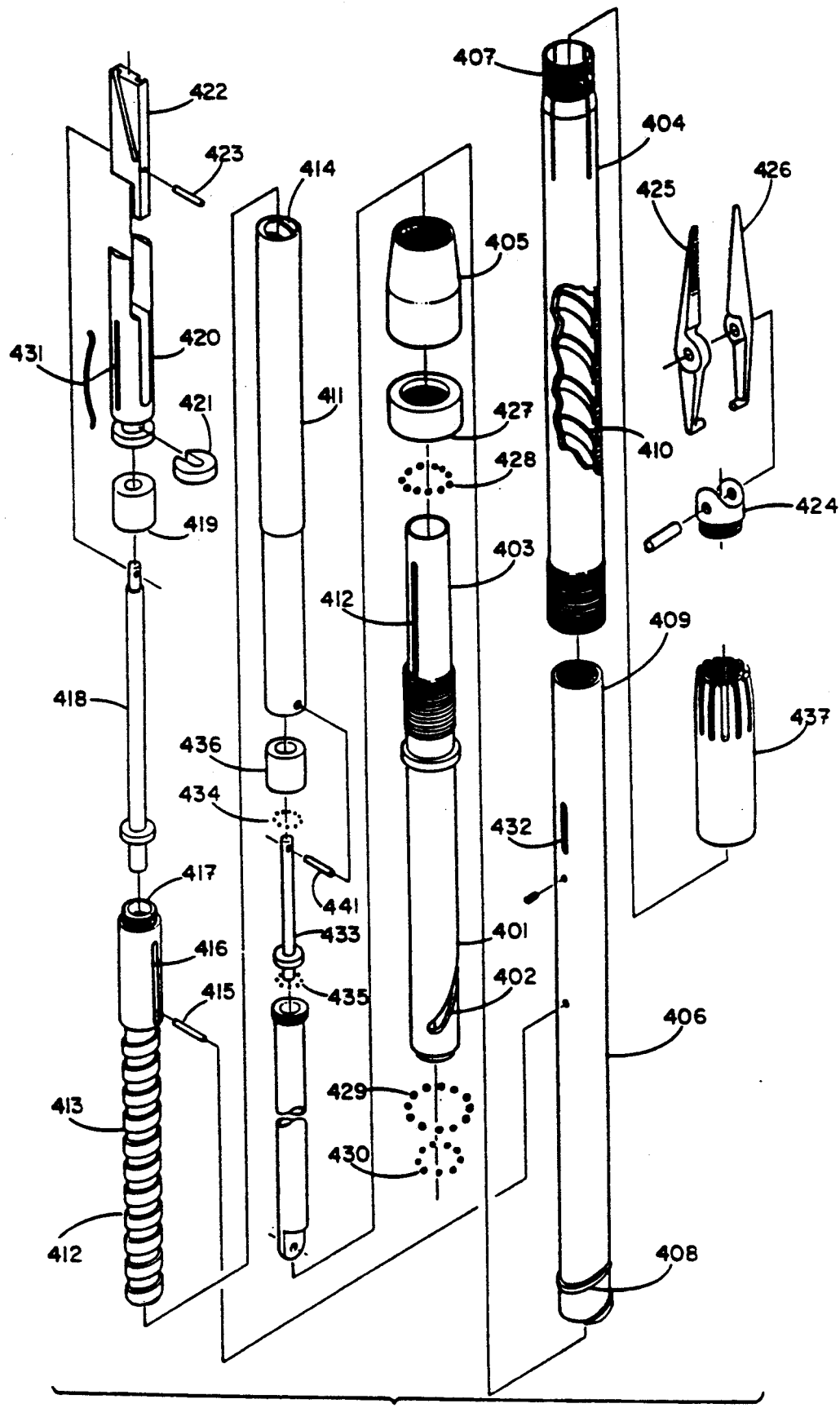
FIG. 11 is an exploded view of an embodiment of the invention which shows the axial extension capability of the instrument.

Turning now to FIG. 11, an embodiment of the invention is shown which permits the user to extend the length of the instrument and thereby advance the end-effector assembly without advancing the proximal end of the instrument. A tube 401 with a spiral groove 402 at the proximal end thereof serves the same function as the corresponding spiral groove 90 on the proximal end 74 of the tube 8 in the embodiment of FIG. 2. Fitting over the distal end 403 of the tube 401 in this embodiment however is a barrel 404, which is secured to the tube 401 by an adaptor nut 405. Passing through the barrel 404 is a hollow spindle 406 which exceeds the barrel in length and protrudes from the distal end 407 of the barrel. The spindle 406 contains a broad thread 408 formed on its exterior surface beginning at the proximal end and extending only a short distance along the spindle. This broad thread is mated with a corresponding thread 410 along the inner surface of the barrel 404, extending substantially the full length of the barrel. A typical pitch of the thread is five threads to the inch. The distal end 409 of the spindle 406 which protrudes from the distal end 407 of the barrel 404 may thus be turned by one's fingers, which will cause the thread 408 on the external surface of the spindle to travel along the thread along the internal surface of the barrel, and thereby cause the spindle to move axially within the barrel.

This axial movement of the spindle 406 relative to the barrel 404 is matched by a corresponding axial movement of smaller diameter elements retained inside the spindle and barrel, which in turn communicate the axial movement to the end-effector assembly. These inner, smaller diameter elements include a hollow draw tube 411 and a draw bar 412 which passes through the draw tube 411. The draw bar 412 has broad threads 413 formed along its outer surface, and these are mated to corresponding broad threads 414 along the inner surface of the draw tube 411. These threads are of the same pitch as the threads 408 on the spindle 406.

A pin 415 affixed to the spindle 406 and extending inward engages a slot 416 on the draw bar, and thus the turning of the spindle causes a simultaneous turning of the draw bar. Since the threads 413 on the draw bar are of the same pitch as the thread 408 on the spindle, the turning of the spindle causes the draw bar to turn at the same rate and advance relative to the draw tube 411 at the same linear rate in the axial direction as the spindle relative to the barrel 407.

At the distal end 417 of the draw bar is an extension rod 418, secured to the draw bar by a threaded nut 419. The components at the distal end of the extension bar are a fork assembly 420, a U-collar 421, a cam block assembly 422, a pin 423, end-effector element pivot 424, and a pair of end-effector elements 425, 426, which are analogous to those of the embodiment shown in FIG. 9A, and operate in the same manner. A locking spring 431 extends outward from the fork assembly 420 to extend into a slot 432 in the spindle. This joins the fork assembly to the spindle.

Secured to the proximal end of the draw tube 411 are a second draw bar 433, two ball bearing races 434, 435, and a nut 436, which are analogous to and function in the same manner as the corresponding elements in the embodiment of FIG. 9A. Other elements included in the structure and associated with the tube 401 containing the spiral groove are a retaining nut 427 and three sets of ball bearings 428, 429, 430. Each of these elements is analogous to and serves the same function as the corresponding retaining nut 166 and ball bearings 162, 160, 220 of the embodiment of FIG. 9A.

A further connecting element is a pin 441 which passes through a longitudinal slot 442 in the spiral groove tube 401, as well as the proximal end of the draw tube 411 and the distal end of the second draw bar 433, keeping these three elements in rotational alignment.

The extension of the end-effector assembly elements is therefore achieved by manually twisting the spindle 406 at a location extending distal to the distal end 407 of the barrel 404. As the spindle and barrel combination are being elongated, the internal draw assembly consisting of the draw bar 412 and draw tube 411 are being elongated at the same rate. This maintains the end-effector elements 425, 426 in harmony with the action of the finger handles, which although not shown in this figure are identical to those shown in FIG. 1. Once the desired extension has been achieved, the spindle 406 may be locked into position relative to the barrel 404 by a clamp nut 437, which compresses the slotted distal end 407 of the barrel down against the spindle. Since the adaptor nut 405 renders the barrel 404 and the spiral groove tube 401 immobile relative to each other, the barrel 404, spindle 406 and spiral groove tube 401 all rotate together once the clamp nut 437 is secured.

Figure 12:
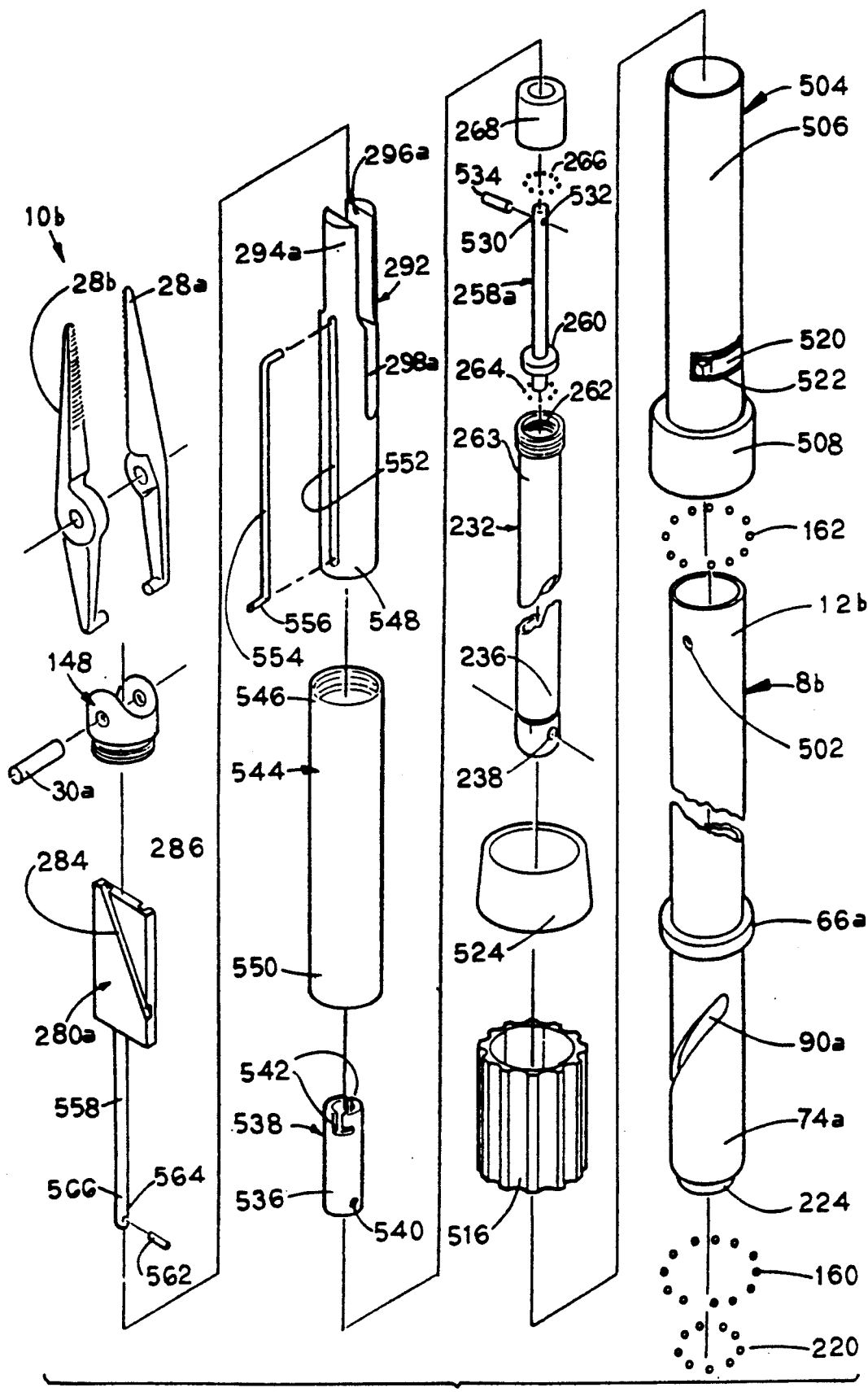
FIG. 12 is an exploded isometric view, similar to FIG. 9A, of the distal portion of an alternative embodiment of the instrument of FIG. 8 in which the user can selectively lock out relative rotary motion between the tube assembly and the body, and also showing a user removable end-effector assembly.
Figure 13:
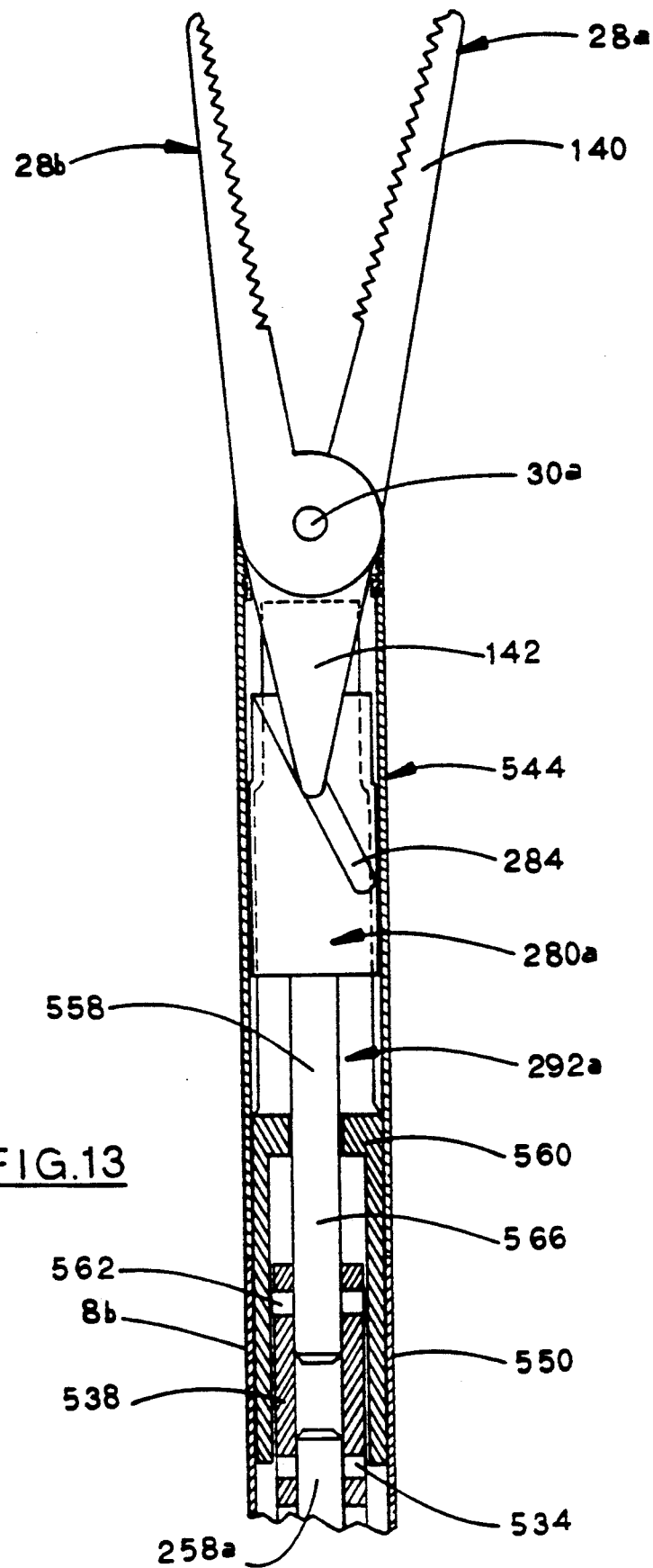
FIG. 13 is an enlarged cross-sectional assembled view of the distal end of the portion of the instrument shown in FIG. 12 with the end-effector elements partially open.
Figure 13A:
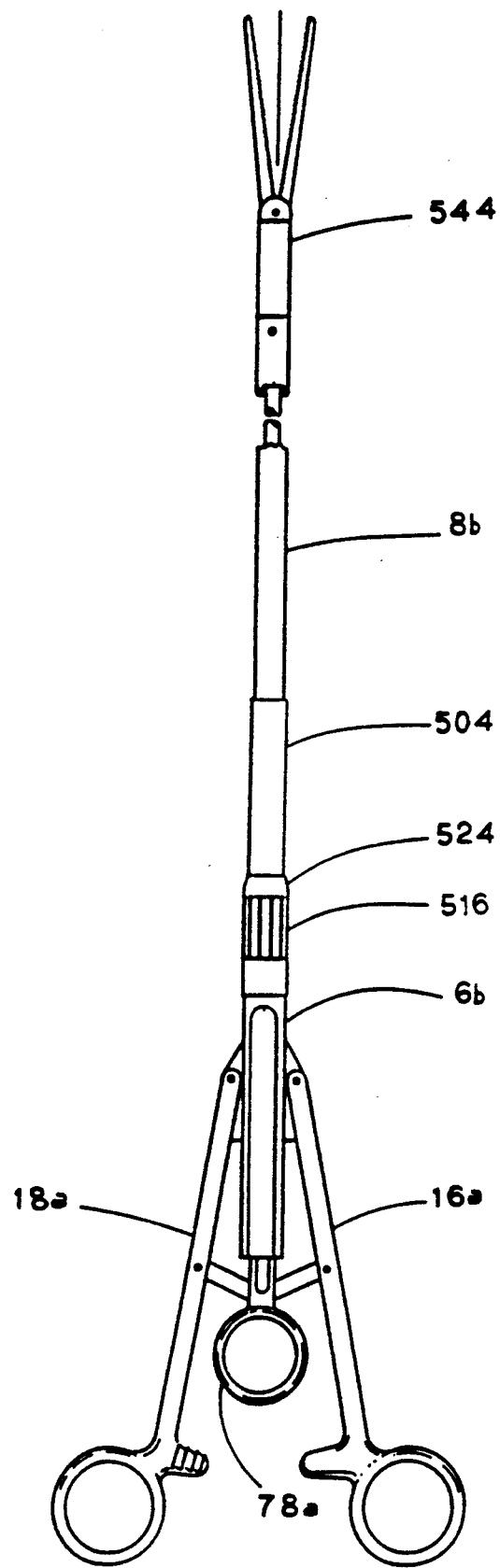
FIGS. 13A and 13B are external views of an alternative embodiment of the instrument of FIG. 8 incorporating the distal portion of FIG. 12 shown in partially open and closed positions.
Figure 13B:
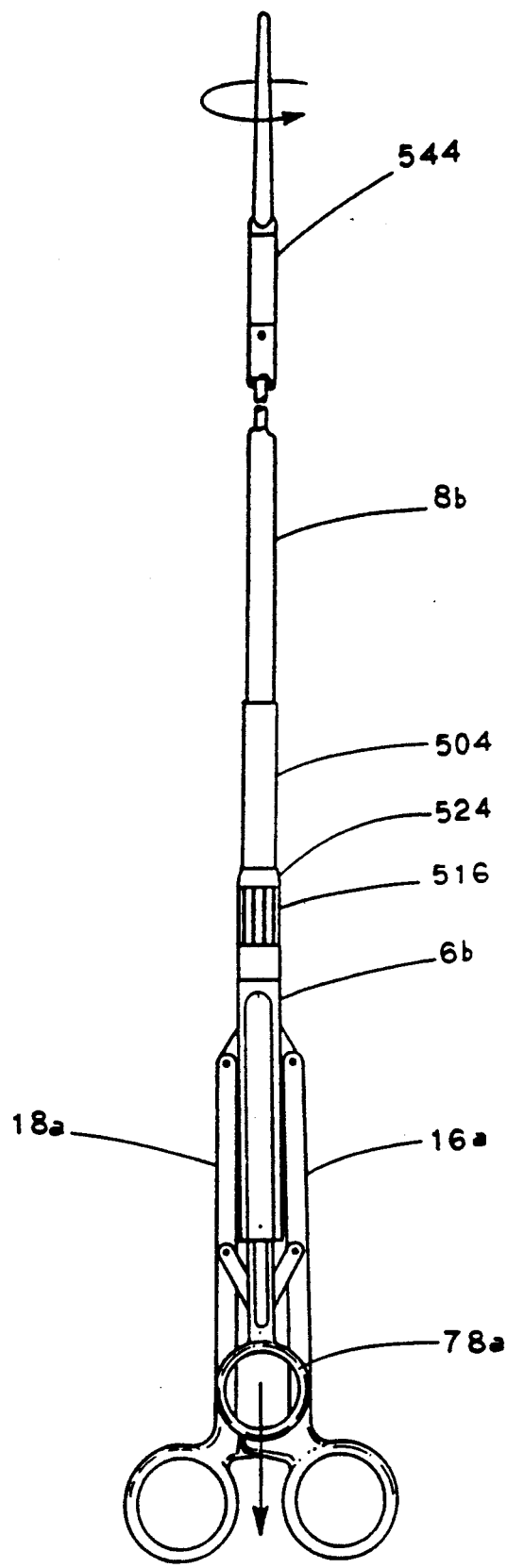
Figure 14:
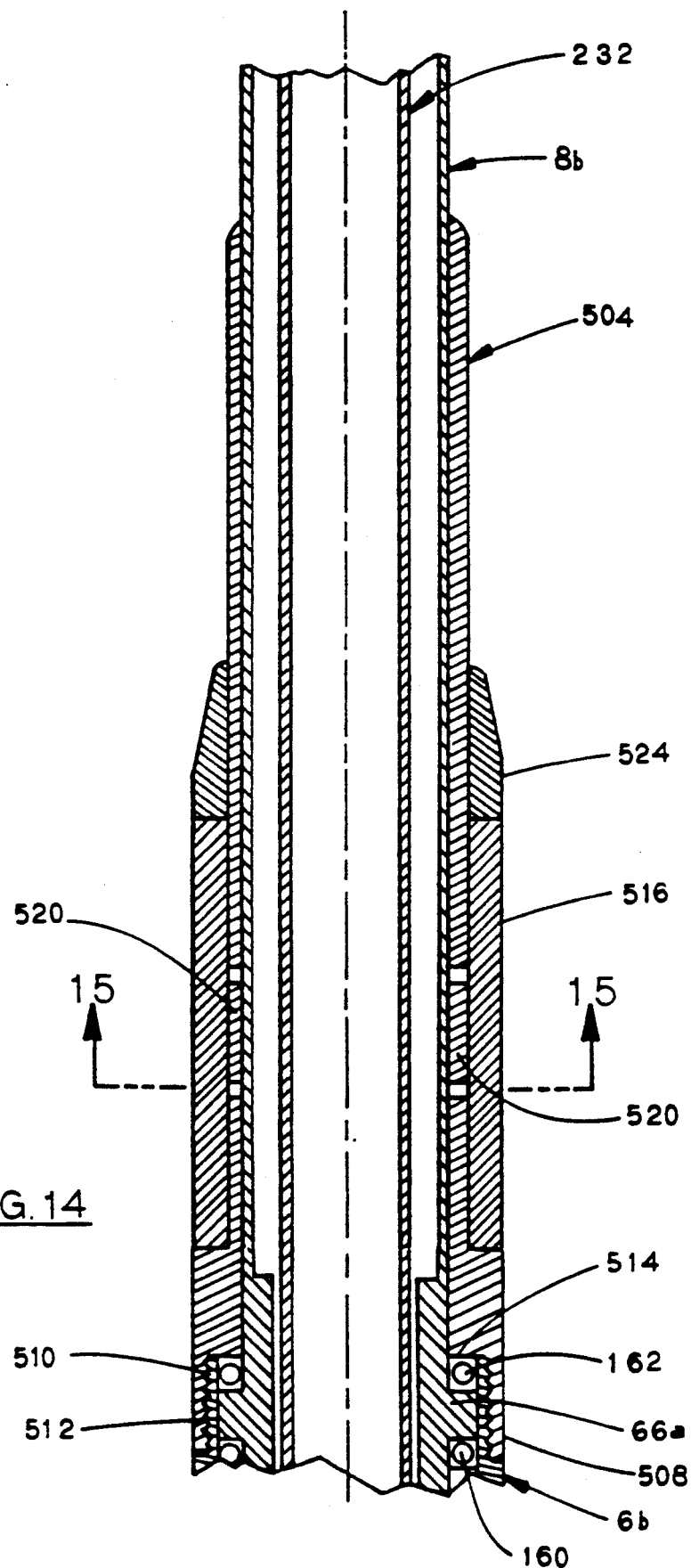
FIG. 14 is an enlarged assembled view of the proximal end of the instrument portion shown in FIG. 12 shown mounted to the base.
Figure 15A:
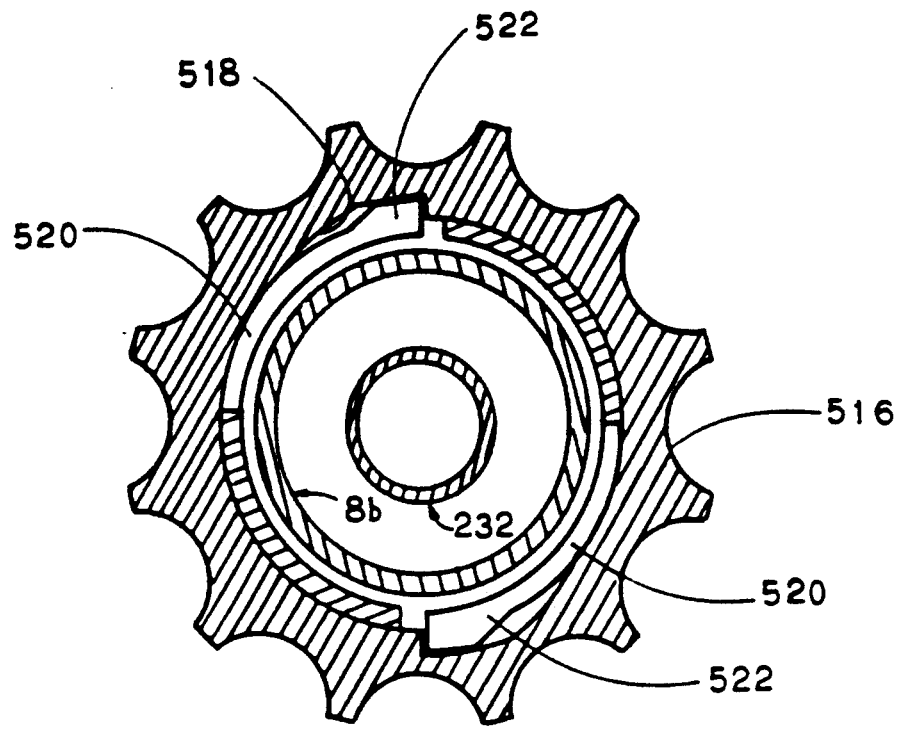
FIGS. 15A and 15B are enlarged cross-sectional views taken along line 15—15 of FIG. 14 showing the serrated lockout collar in its free movement position in FIG. 15A, which allows the end-effector assembly to rotate freely relative to the body, and the rotary motion lockout position of FIG. 15B, showing the frictional engagement of the lockout fingers, formed as part of the base extension, with the end-effector carrier tube thereby preventing the end-effector carrier tube, and the end-effector assembly therewith, from rotating relative to the base.
Figure 15B:
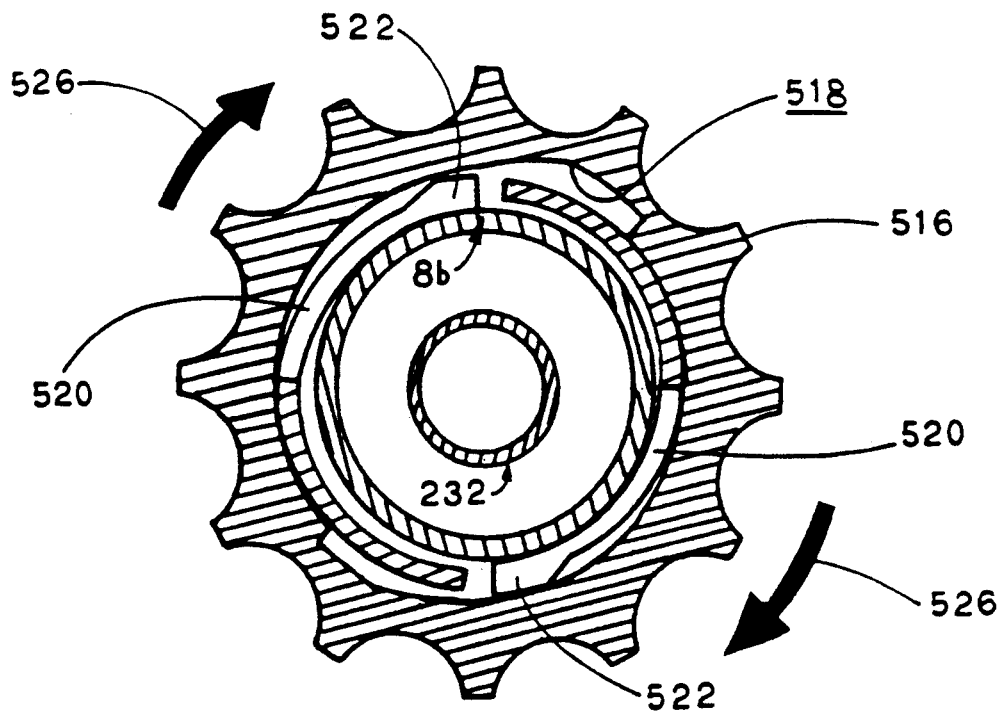

FIGS. 12-15 relate to a further embodiment of the invention in which the distal portion, shown in FIG. 9A, of instrument 2b, shown in FIGS. 13A and 13B, has been modified. The purposes for the modifications are to permit the user to selectively lockout or prevent rotary motion of the end-effector elements relative to the base and also to permit the user to easily and quickly replace one end-effector assembly with another end-effector assembly. Many of the elements are the same as or similar to those described above; these elements will not be described in detail but will be referred to with like reference numerals.

End-effector carrier tube 8b is similar to end-effector carrier tube 8a but lacks internal threads 154 and has a circular hole 502 instead of slot 314. The purpose of hole 502 will be described below. Base extension 504 is secured to base 6b (see FIG. 14) and acts as an extension of base 6b. Base extension 504 includes an elongate cylindrical portion 506 and a bearing end 508. Bearing end 508 has internal threads 510 which engage external threads 512 formed at the distal end of base 6b. Accordingly, base extension 504 is a one-piece, rigid extension of base 6b and thus does not rotate or move axially relative to the base. Bearing end 508 also helps to capture a set of ball bearings 162 between an internal shoulder 514 formed at bearing end 508 and annular shoulder 66a formed as a part of end-effector carrier tube 8b.

Due to the presence of sets of ball bearings 160, 162, end-effector carrier tube 8b can rotate relative to base 6b and base extension 504. This relative rotary motion can be prevented through the use of a serrated lockout collar 516. Serrated lockout collar 516 has a pair of internal cam surfaces 518 which lie opposite a pair of resilient lockout fingers 520. Lockout fingers 520 have cam bumps 522 formed at their distal ends which engage internal cam surfaces 518. Collar 516 is held in a fixed position axially along base extension 504 by a retainer band 524 which is press fit over cylindrical portion 506 of base extension 504. When lockout collar 516 is at the free movement position of FIG. 15A, lockout fingers 520 are spaced apart from end-effector carrier tube 8b so that end-effector carrier tube 8b can move freely within base extension 504. However, rotating lockout collar 516 in the direction of arrows 526 to the rotary motion lockout position of FIG. 15B causes lockout fingers 520 to press tightly against end-effector carrier tube 8b, thus frictionally securing the end-effector carrier tube to base extension 504 and thus to base 6b.

Axial drive 232 has a flanged drawbar 258a mounted to its distal end 263 by capturing flange 260 between sets of ball bearings 264, 266. Drawbar retaining nut 268 passes over flanged drawbar 258a and is threadably secured to the threads at end 263.

The distal end 530 of flanged drawbar 258a has a lateral hole 532 formed therethrough. Hole 532 is sized to accept a pin 534 to permit distal end 530 to be secured to the proximal end 536 of a bayonet receptacle 538. Receptacle 538 is a generally cylindrical member having a laterally extending hole 540 at its proximal end 536 sized for receipt of pin 534. Bayonet receptacle 538 has a pair of L-shaped slots 542. These L-shaped slots are used for engaging the end-effector assembly 10b as is discussed below.

End-effector assembly 10b includes the rest of the structure shown in FIG. 12 and not yet discussed. End-effector assembly 10b includes an end-effector tube 544 having an internally threaded distal end 546 to which end-effector coupler plug 148 is threadably secured. End-effector assembly 10b also includes a fork 292a which is mounted to the interior of end-effector tube 544 through a press fit. Fork 292s is sized so that the proximal end 548 of fork 292a extends past proximal end 550 of end-effector tube 544. Fork 292a includes an axially extending slot 552 sized to accept a generally Z-shaped catch spring 554. The proximal end 556 of catch spring 554 is a radially extending end-effector which extends out past the outside surface of end-effector tube 544. The proximal end 548 of fork 292a is sized to fit within end-effector carrier tube 8b so that proximal end 556 of catch spring 554 can engage hole 502 formed in the end-effector carrier tube. Doing so retains end-effector tube 544 and fork 292a therewith in position both axially and radially relative to end-effector carrier tube 8b.

As discussed above, cam block 280a is mounted within wider gap 296a of fork 292a. Cam block 280a includes a cam block extension 558 which passes through and is guided by an internal shoulder 560 (see FIG. 13) formed within fork 292a. A bayonet pin 562 passes thorough a lateral bore 564 formed in the proximal end 566 of guide block extension 558. Pin 562 engages L-shaped slots 542 to permit end-effector assembly 10b to be mounted to and disengaged from the remainder of the instrument.

End-effector assembly 10b includes broadly end-effector tube 544, fork 292a, cam block 280a, end-effector coupler plug 148 and end-effector elements 28a, 28b. To mount an appropriate end-effector assembly 10b to the remainder of instrument 2b, the user inserts cam block extension 558 and proximal end 548 of fork 292a through the distal end 12b of end-effector carrier tube 8b until bayonet pin 562 contacts bayonet receptacle 538. Bayonet receptacle 538 is held in place by flanged drawbar 258a. The user then rotates end-effector assembly 10b until bayonet pin 562 becomes aligned with the axially extending portions of slots 542. The user than pushes end-effector assembly 10b axially and then twists the end-effector assembly until bayonet pins 562 engage the circumferentially extending portions of slots 542. When this occurs, proximal end 556 of catch spring 554 becomes aligned with and moves into hole 502, thus securing end-effector assembly 10b in place. When it is desired to replace end-effector assembly 10b; for example, if a different type of end-effector elements 28a, 28b is needed, the user inserts a tool into hole 502 to depress proximal end 556 of catch spring 554. The user then rotates end-effector assembly 10b to align bayonet pin 562 with the axially extending portions of slots 542 and then pulls end-effector assembly 10b out of end-effector carrier tube 8b. The replacement end-effector assembly can then be mounted within end-effector carrier tube 8b. If during use the user desires to prevent end-effector assembly 10b from rotating relative to base 6b, the user merely rotates lockout collar 516 in the direction of arrows 526.

Figure 9B:
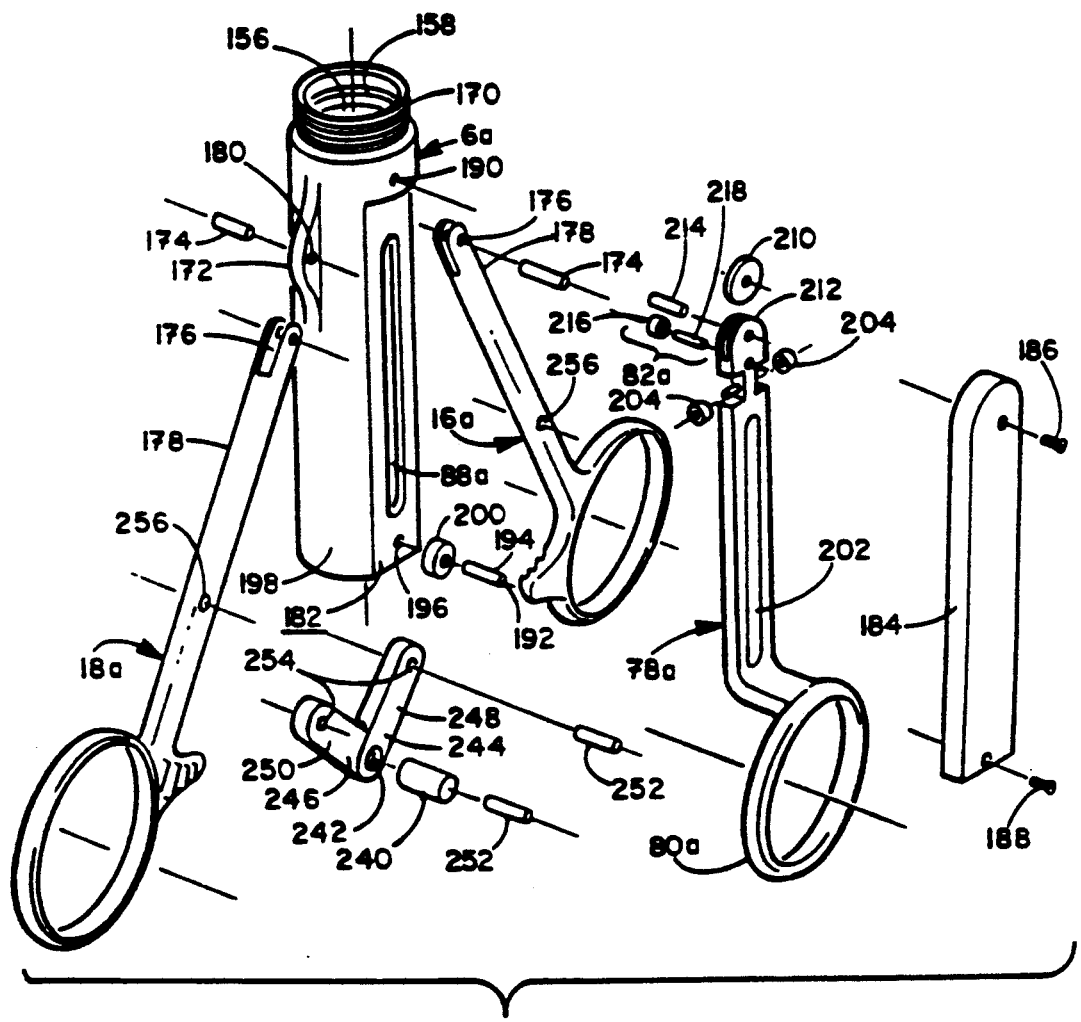

Other types of mechanisms can be used to keep end-effector carrier tube 8b from rotating relative to base 6b. Various types of clamps or thumbscrews could be used. With reference to FIG. 9B, rotary actuator trigger 78a could have a serrated surface along its length, and base 6a could include some type of catch or keeper along slot 88a which could be actuated to engage the serrated surface along trigger 78a, thus locking the trigger in place.

Other modification and variation can be made to the embodiments disclosed. For example, other methods for mounting an end-effector assembly to the remainder of the device could be used as well. It may be desired to spring bias rings 16, 18 away from one another and trigger 78 towards the position of FIG. 1.

The present invention is particularly directed to an endoscopic surgical instrument of the type discussed above which has a smooth, nonrotating exterior between its end-effector and the base to minimize friction between the instrument and the surrounding tissue during use and to prevent exterior ledges, annular steps and the like from interfering with the tissue and tearing or otherwise traumatizing the surrounding tissue during use and, especially, during the insertion and withdrawal of the instrument. The invention further provides an improved manner for replacing instrument end-effectors as compared to the embodiment illustrated in FIGS. 2–14 hereof and described above.

Referring now to FIGS. 16-22B, an endoscopic surgical instrument 602 of the present invention uses the same base and actuating mechanism 604 as previously described and shown with particular clarity in FIGS. 9B and 10B. Thus, the actuating mechanism includes a driver assembly 606 for moving end-effector elements 608, 610, such as a pair of jaws, of end-effector assembly 607 between their open and closed positions, and an end-effector element rotator assembly 612 for rotating the end-effector element assembly, and therewith the end-effector elements about the axis 614 of the instrument.

More specifically, and as described in greater detail above, the driver assembly includes finger and thumb rings 616, 618 which are pivotally attached to lugs 620 of an instrument base 622. By moving the finger and thumb rings towards and away from each other, a cam drive rod 624 is axially translated towards and away from the end-effector elements to open and close them in a manner further described below.

The end-effector element rotator assembly 612 includes a trigger 626 which includes a trigger ring 628 and which is axially translatably mounted to the exterior of base 622. Movement of the trigger in an axial direction rotates an annular spindle 630 (which surrounds end-effector element drive rod 624) via a cam pin (not separately shown in FIGS. 17-22) and a spiral groove 632 (see FIG. 19) in the spindle as described in detail above and particularly well illustrated in FIGS. 9B and 10B.

Figure 18:
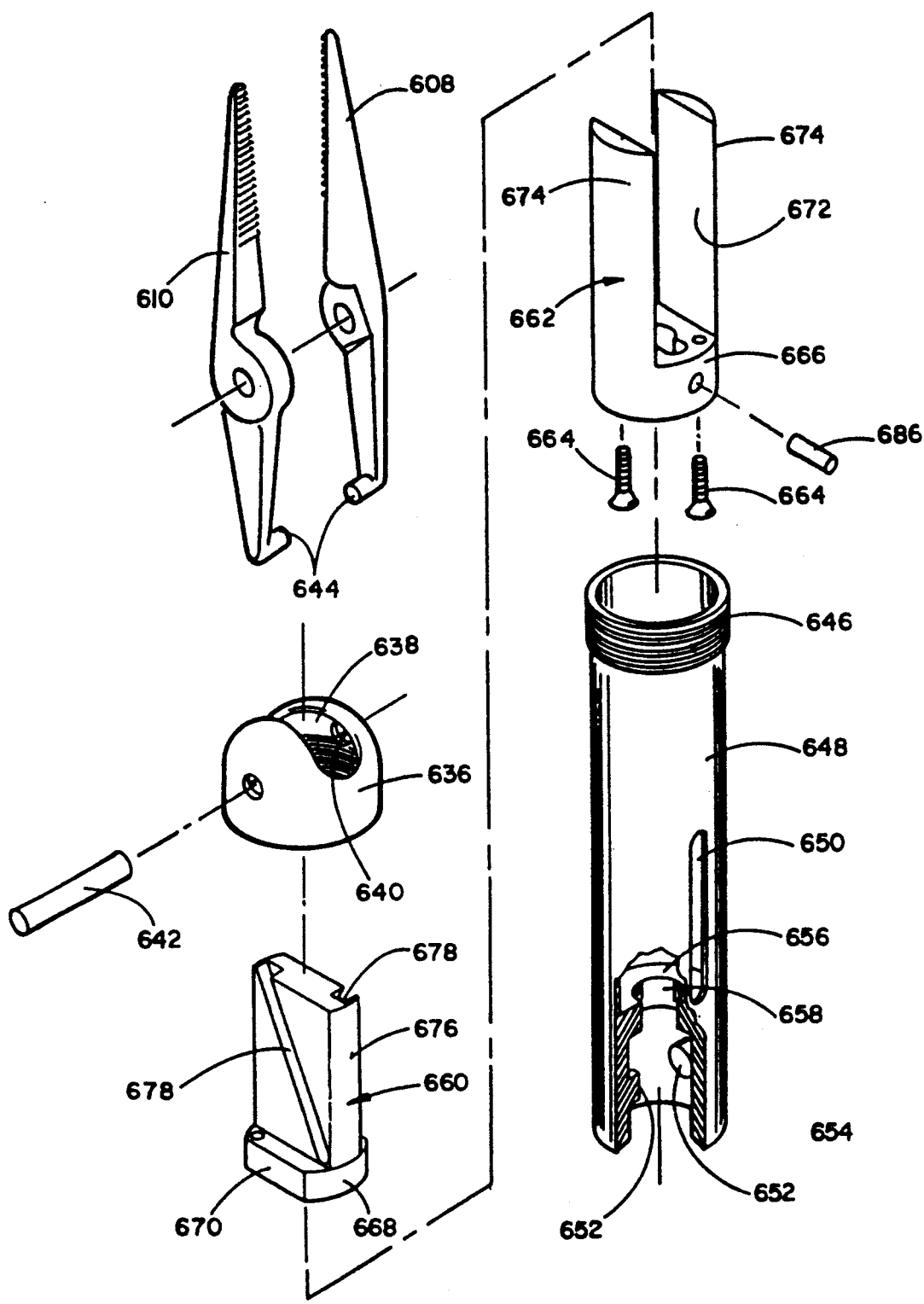
FIG. 18 is an exploded, perspective view, with parts in section, of an end-effector assembly constructed in accordance with the present invention.

Referring now to FIG. 18, end-effector assembly 607 includes a hemispherical nut 636 which has an upwardly oriented slot 638 (through which end-effector elements 608, 610 protrude), an internal thread 640, and a pin 642 which pivotally mounts the end-effector elements to the nut. As earlier described, the end-effector elements include inwardly oriented cam followers 644. The hemispherical nut engages an external thread 646 on an elongated end-effector element sleeve 648 which also includes an elongated slot 650 for purposes further described below. A pair of opposing, inwardly directed pins 652 are located in the vicinity of a proximal end 654 of the end-effector element sleeve. The end-effector element sleeve includes an interior, annular flange 656 which defines a central opening 658 through which the earlier mentioned end-effector element drive rod 624 (not shown in FIG. 18) extends.

Figure 20:
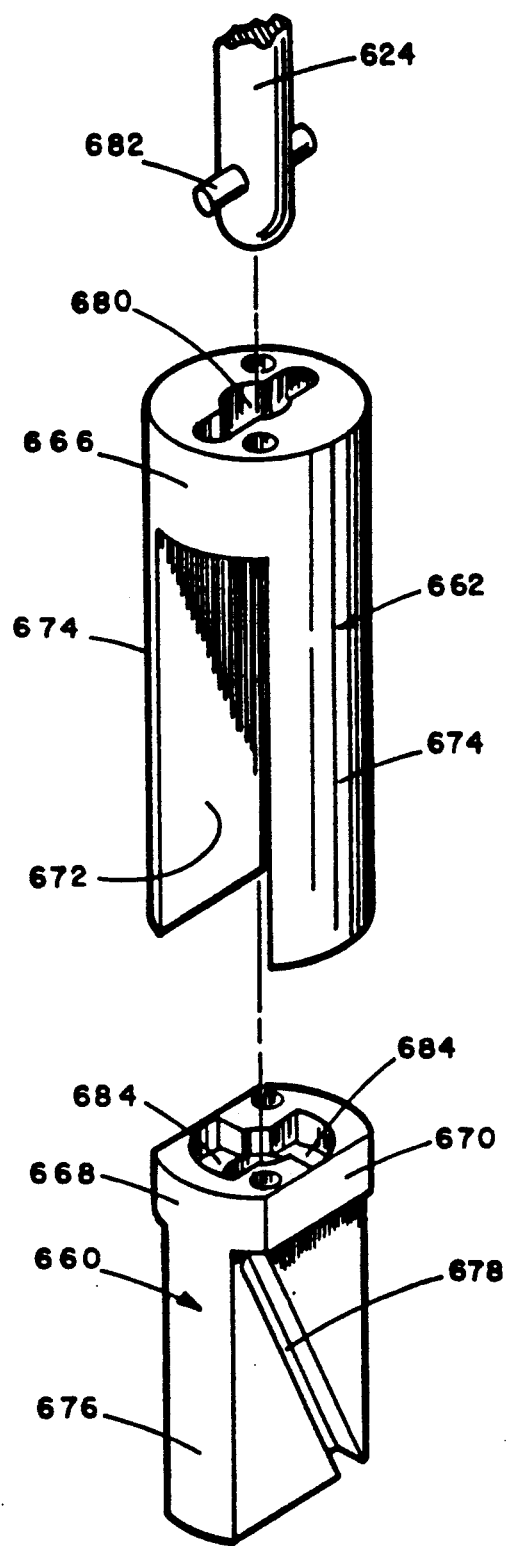
FIG. 20 is an exploded, fragmentary, perspective view illustrating the connection between the end-effector drive rod, the end-effector cam block, and the end-effector cam block holder.
Figure 21:
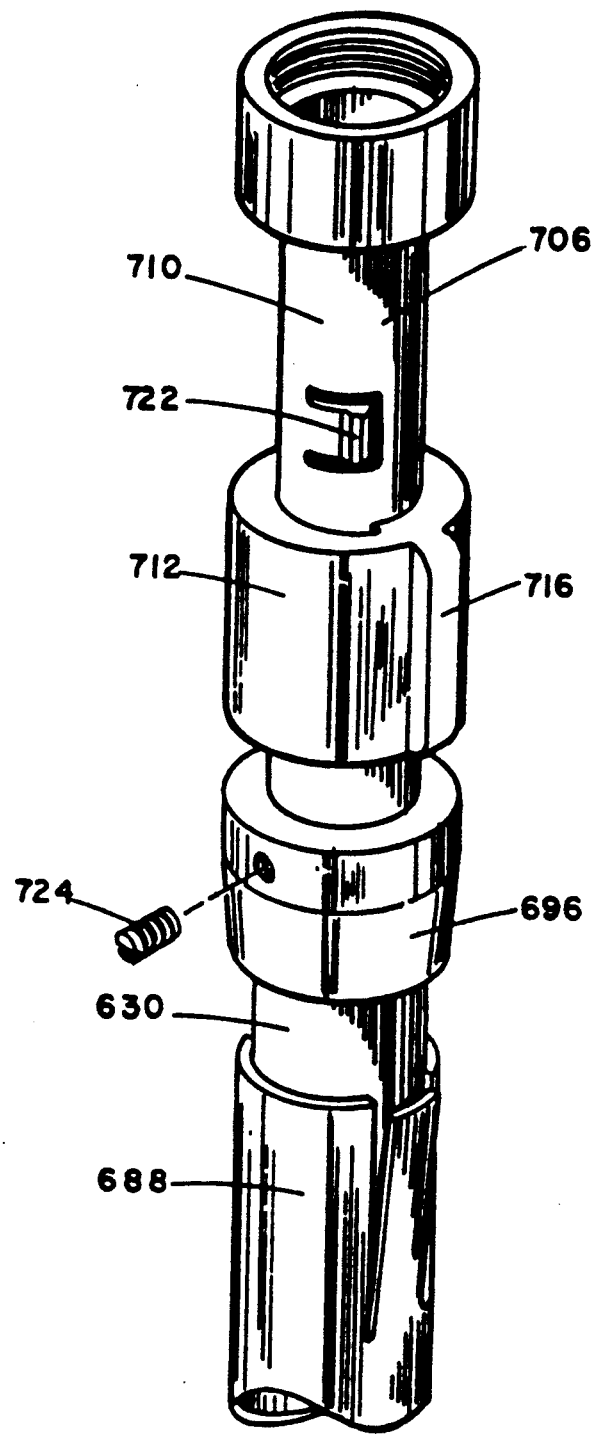
FIG. 21 is a fragmentary, perspective and partially exploded view illustrating the proximal end of that portion of the instrument of the present invention which connects to the base.

Referring now to FIGS. 18 and 20, with hemispherical nut 636 threaded onto the distal end of end-effector element sleeve 648, a cam block 660 secured to a forked holder 662 with screws 664 is disposed in the space between the nut and inner flange 656 of the end-effector element sleeve. The screws extend through corresponding holes in a base 666 of the holder and are threaded into threaded holes in a base flange 668 of the cam block. The flange of the cam block has flat faces 670 which are dimensioned so that they fit between opposing faces 672 of fork blades 674 of holder 662. A relatively narrow main body 676 projects upwardly from base 668 of the cam block and includes diagonally oriented grooves 678 for slidably receiving the opposing cam followers 644 of end-effector elements 608, 610.

The base 666 of the cam holder includes a central hole 680 through which end-effector element drive rod 624 can extend and a pair of opposite slots extending therefrom so that a bayonet pin 682 at the distal end of the drive rod can be passed therethrough (see FIG. 17). The bottom end of cam block flange 668 includes a central opening which is coaxial with opening 680 in base 666 of the holder 662 and a pair of opposing, pie-shaped cut-outs 684 which extend over an arc of about 90°. Thus, when the cam block is secured to the forked holder with screws 664, end-effector element drive rod 624 can be operatively connected thereto by initially aligning bayonet pin 682 with the slots in base 666 of the holder, axially advancing the rod until the bayonet pin is disposed within the pie-shaped cut-out in the base of the cam block and thereafter rotating the cam block relative to the drive rod, which disaligns the bayonet pin with the slots in the holder and thereby couples the rod to the holder and to the cam block.

Forked holder 662 also includes a pin 686 which protrudes radially outwardly and extends through slot 650 in end-effector element sleeve 648 and permits limited axial movement of the holder, and therewith the cam block, within the confines of the slot and prevents relative rotation between the holder, and therewith the end-effector assembly, and the end-effector element sleeve.

Figure 19:
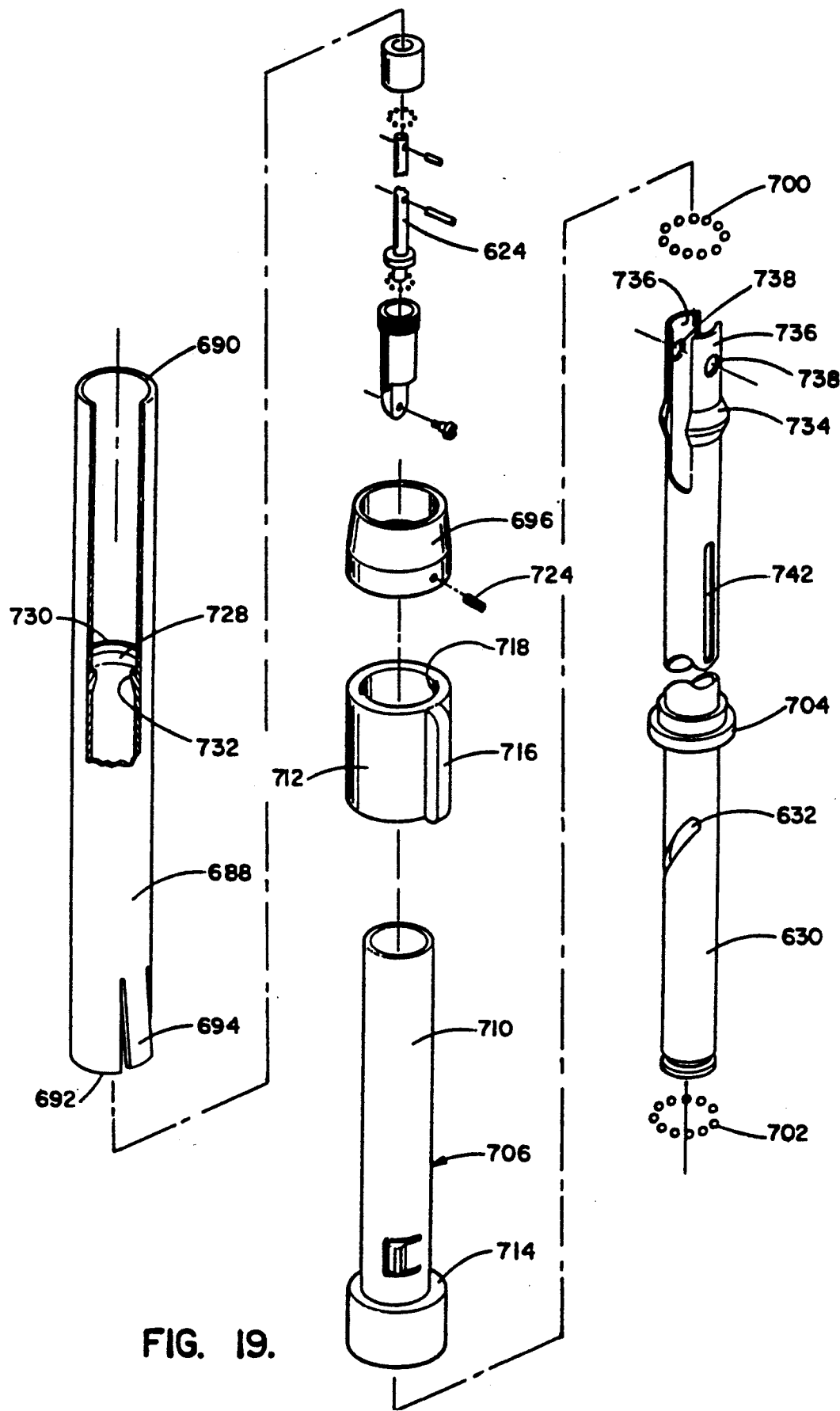
FIG. 19 is a perspective, exploded view, partially in section, of the portion of the instrument between its base and the end-effector assembly (without showing the end-effector assembly itself)

Referring now particularly to FIGS. 17 and 19, a nonrotatable, tubular housing 688 has a distal end 690 which engages a shoulder (best seen in FIG. 17A) defined by the end of hemispherical nut 636. A proximal end 692 of the tubular housing includes a pair of opposite, outwardly protruding spring tabs 694 which engage the end face of a tubular keeper band 696 that has a frusto-conical exterior shape. The housing surrounds the earlier mentioned, tubular spindle 630 which is rotatably secured to a distal end 698 of base 622 with two sets of ball bearings 700, 702 disposed on opposite sides of a radial flange 704 protruding from the spindle. An extended, tubular nut 706 threadably engages a threaded end 708 of base 622 and forms the required constraint for bearings 700, 702. Nut 706 has a tubular extension 710 of sufficient length so that it extends well past keeper band 696 and spring tabs 694.

Figure 22A:
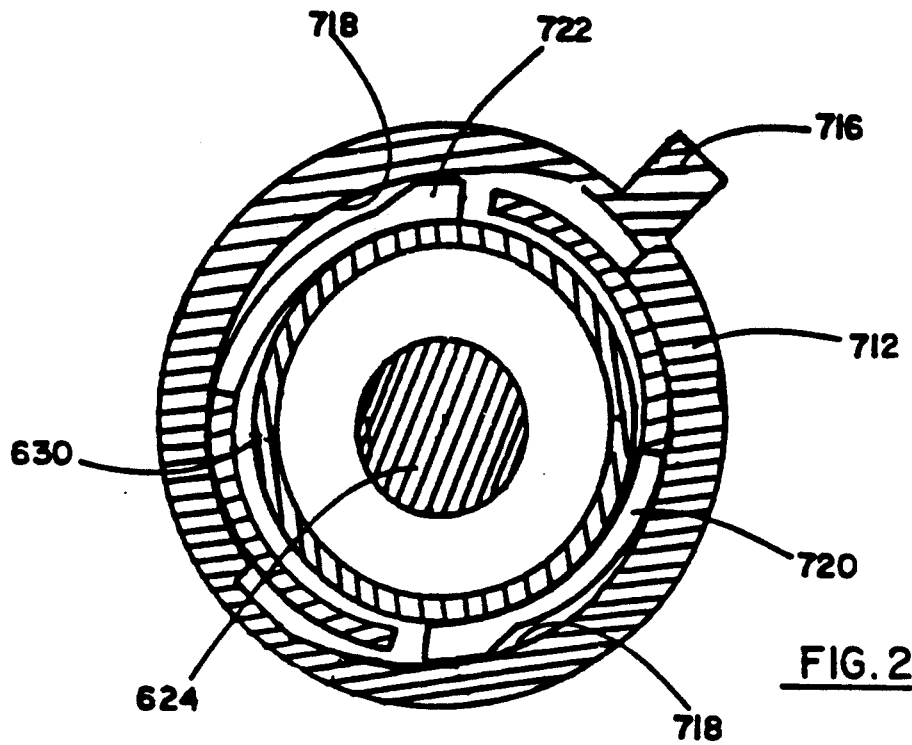
FIGS. 22A and 22B are cross-sectional views taken along line 22—22 of FIG. 17 and illustrate the mechanism for frictionally locking the end-effector assembly mounting spindle against rotational movements.
Figure 22B:
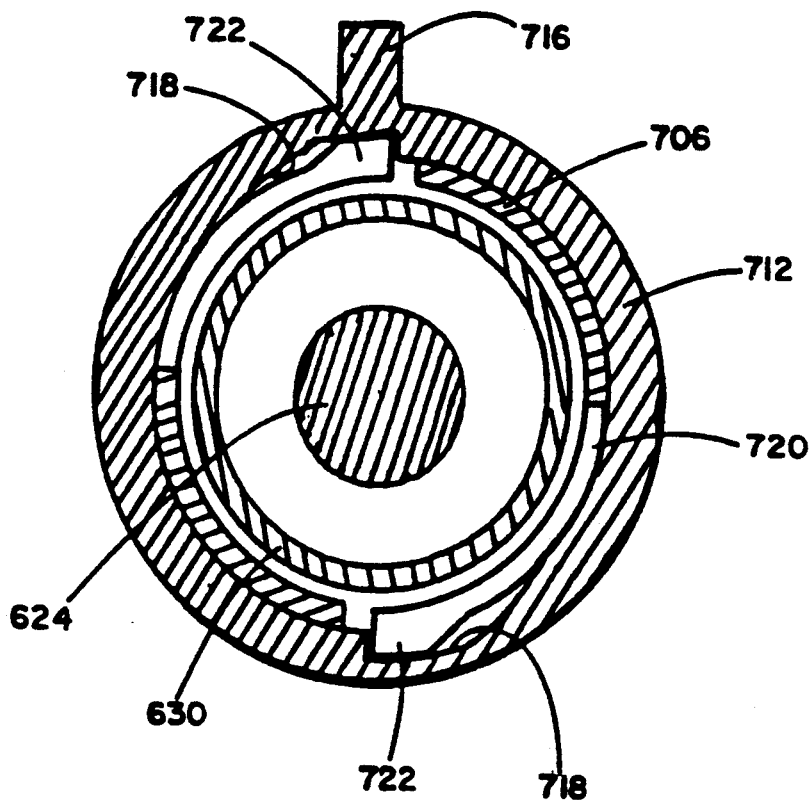

A rotary lock collar 712 surrounds the tubular nut extension 710 and is located in the space between the proximal end of keeper band 696 and a shoulder 714 of the extended tubular nut 706. The lock collar includes an axially extending actuating flange 716 (best seen in FIGS. 22A and 22B) and defines, on its interior cylindrical wall, a pair of internal cam surfaces 718 which lie opposite a pair of resilient, circumferential locking fingers 720 formed by appropriately slitting the tubular extension 710 of nut 706. The fingers include cam bumps 722 which extend into the cam surfaces of the rotary lock collar 712. By rotating the lock collar in a counterclockwise direction (as seen in FIG. 22B), the cam bumps on the fingers are engaged by the internal cam surfaces and pressed radially inward to frictionally engage tubular spindle 630 (as shown in FIG. 22A) and thereby lock the spindle against rotational movements. Rotation of the lock collar from its locking position, as seen in FIG. 22A, in a clockwise direction, as seen in FIG. 22A, releases the friction lock.

Keeper band 696 is secured to the tubular nut 706 with a set screw 724. The distal end of the keeper band includes an enlarged-diameter cylindrical surface 726 (see FIG. 17) to define an annular recess between it and the tubular extension 710 of the nut which is open in a distal direction. The annular space has sufficient width so that it can receive the end of tubular housing 688. In use, spring tabs 694 at the proximate end of the housing prevent the housing from entering the annular space. However, upon depressing the tabs flush with the remainder of the tubular housing, it can be retracted into the annular space for purposes further discussed below.

On the interior of tubular housing, relatively closer to its distal end, is an inwardly protruding compression ring 728 which defines a shoulder 730 facing towards the distal end of the housing and a sloped surface 732 which faces towards the proximal end 692 of the housing. The compression ring cooperates with a radially outwardly protruding, double-tapered flange 734 on tubular spindle 630. The distal end of the spindle is axially slotted past flange 734 to define a pair of opposing spindle arms 736 which can be resiliently moved towards each other. Aligned holes 738 are formed in the spindle, arm for engaging the inwardly extending pins 652 (see FIG. 18) at the proximal end 654 of end-effector element sleeve 648.

When fully assembled and in its operative position, best illustrated in FIG. 17, flange 734 on spindle arms 736 is located closely adjacent to compression ring 728 on the inside of stationary housing 688. In this position, the inwardly protruding pins 652 on end-effector element sleeve 648 engage the holes 738 in the spindle arms and thereby secure the end-effector element sleeve and therewith movable end-effector elements 608, 610. The end-effector element sleeve can be compressing spring tabs 694 at the proximate ends of stationary housing 688 and then axially pulling the housing into the annular space between keeper band 696 and the tubular extension 710 of nut 706. In the process of pulling the housing into the annular space, the sloped surface 732 of compression ring 728 engages the flange 734 on spindle arms 736 and thereby resiliently forces the arms inwardly. This inward deflection of the arms disengages pins 652 from holes 738 in the spindle arms so that the end-effector element sleeve can be separated from the spindle by grasping it and moving it away therefrom in an axial direction.

Figure 16:
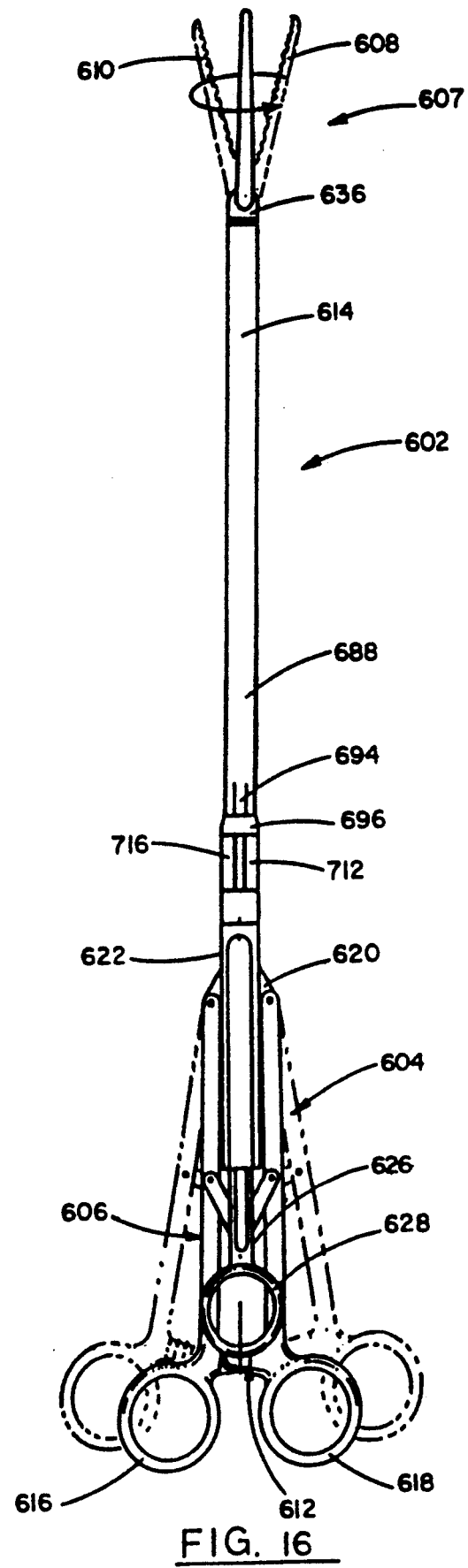
FIG. 16 is a plan view of the endoscopic surgical instrument of the present invention and shows, in phantom lines, the relative position of the various parts of the instrument when the end-effector elements are open.

Summarizing the operation of the endoscopic surgical instrument 602 illustrated in FIGS. 16–22, and assuming that end-effector assembly 607 has been operatively connected to end-effector element drive rod 624 and tubular spindle 630, the finger and thumb rings 616, 618 of the driver assembly 606 are initially in their "closed" position (illustrated in FIG. 16) at which the rings are proximate to each other and end-effector elements 608, 610 are closed. The end-effector element rotator assembly may be in any desired position with trigger ring 628 in the position, for example, in which it is shown in FIG. 16. At this point, spring tabs 694 engage the distal end of keeper band 696. The distal end of the tubular housing 688 engages the shoulder of hemispherical nut 636 and forms therewith a bearing surface permitting the nut to rotate relative to the housing. To reduce friction, the bearing surface may include a low-friction; e.g. Teflon, coating.

To open the end-effector elements, the finger and thumb rings 616, 618 are spread apart. Upon spreading them, the arms to which the rings are attached pull end-effector element drive rod 624 rearwardly (downwardly as seen in FIG. 16) via actuating mechanism 604, the details of construction and operation of which were described above. As the rod is pulled rearwardly, the bayonet pin 682 at the distal end of the rod pulls holder 662 and cam block 660 attached thereto with it. Since the hemispherical nut 636 is threaded onto end-effector element sleeve 648 (which is axially stationarily attached to spindle 630), cam followers 644 on end-effector elements 608, 610 move along the diagonal grooves 678, which causes the end-effector elements to pivot about pin 642 away from each other into an open position. By pushing the thumb rings 616, 618 together, the end-effector element drive rod 624 is axially moved in the opposite direction to thereby close the end-effector elements.

To rotate the end-effector elements about axis 614, trigger ring 628 is moved in one or the other direction relative to base 622. The end-effector element rotator assembly 612 translates this linear movement of the trigger ring into a rotational movement via an operating mechanism, the construction and operation of which was described in more detail above. This rotational movement is imparted to tubular spindle 630 in the manner earlier described. A transverse pin 740 in the drive rod extends into slots 742 in the spindle to rotate the rod with the spindle and to prevent relative rotation between the two. The rotational movement of spindle 630 is transferred to end-effector element sleeve 648 via spindle arms 736 and inwardly oriented pins 652. Rotational movements of the end-effector element sleeve result in corresponding rotational movements of hemispherical nut 636 and end-effector elements 608, 610 because the hemispherical nut is threaded onto the distal end of the end-effector element sleeve.

It will be observed that neither the opening or closing of the end-effector elements, nor their rotation, results in relative movements of tubular housing 688. Thus, neither of the two movements generates friction, which facilitates the use of the instrument. Moreover, the one-piece, tubular housing has a smooth, uninterrupted, constant-diameter exterior, which facilitates the insertion and withdrawal of the instrument through incision, lumen or of tissue, thereby preventing possible tear of or trauma in the tissue surrounding the instrument.

To remove the end-effector assembly 607; e.g. for cleaning or to replace it with a differently constructed end-effector assembly, resilient tabs 694 at the proximate end of tubular housing 688 are compressed. Once the tabs are aligned with the annular space between keeper band 696 and annular extension 710 of nut 706, the housing is pulled back, so that it extends into the annular space. This resiliently compresses spindle arms 736 (because of the interengagement of compression ring 728 and flange 734), disengages the spindle arms from end-effector element sleeve pins 652. The end-effector assembly is now manually rotated relative to drive rod 624 until the bayonet pin 682 is aligned with the slots in holder base 668. The end-effector assembly can now be withdrawn in an axial direction. Thereafter, a new end-effector assembly may be inserted into the distal end of housing 688. The holes 738 in the spindle arms are aligned with the end-effector element sleeve pins 652, and the housing is pulled forwardly (towards end-effector elements 608, 610) to release the spring arms so that they engage the end-effector element sleeve pins 652, thereby locking the end-effector assembly to the spindle.

It will be observed that when the end-effector assembly is removed, housing 688 can be axially slipped off spindle 630 to provide access to the latter to facilitate the cleaning and sterilization of the instrument.

What is claimed is:

1. A surgical instrument comprising:
 a body including a base and a tubular extension, the base defining a proximal end of the body, and the extension defining a distal end thereof;

an end-effector assembly mounted to the distal end of the tubular extension and including at least one movable end-effector element;

an end-effector element driver assembly on the base including a user manipulatable movable end-effector element actuator and means coupling the actuator with the movable end-effector element for moving the movable end-effector element relative to the body;

an end-effector assembly rotator including a user manipulatable rotary actuator on the base and means for drivingly coupling the rotary actuator and the end-effector assembly for rotation of the end-effector assembly relative to the body; and release means for decoupling the end-effector assembly from the end-effector element driver assembly and the end-effector assembly rotator, the release means including means for axially moving the tubular extension relative to the base.

2. A surgical instrument according to claim 1 wherein the release means is operable from the vicinity of the proximal end.

3. A surgical instrument comprising:

a body including a base and a tubular extension, the base defining a proximal end of the body, and the extension defining a distal end thereof;

an end-effector assembly mounted to the distal end of the tubular extension and including at least one movable end-effector element;

an end-effector element driver assembly on the base including a user manipulatable movable end-effector element actuator and means coupling the actuator with the movable end-effector element for moving the movable end-effector element relative to the body;

an end-effector assembly rotator including a user manipulatable rotary actuator on the base and means for drivingly coupling the rotary actuator and the end-effector assembly for rotation of the end-effector assembly relative to the body;

release means operable from the vicinity of the proximate end for decoupling the end-effector assembly from the end-effector element driver assembly and the end-effector assembly rotator; and the tubular extension including a smooth, uninterrupted cylindrical surface extending from proximate the base to proximate the movable end-effector element of the end-effector assembly.

4. A surgical instrument according to claim 3 wherein the end-effector assembly includes first and second portions, the first portion being disposed within the tubular extension and the second portion of the end-effector assembly including the movable end-effector element and a member movably mounting the movable end-effector element, with only parts of the movable end-effector element and the member being disposed outside the tubular extension, and including means permitting relative rotational movements between the tubular extension and the member.

5. A surgical instrument comprising:

a main body formed by a base and an open-ended tubular housing connected with the base, a free end of the tubular housing defining a distal end of the body, and the base defining a proximal end of the body;

an end-effector assembly including a member, at least one movable end-effector element pivotally mounted to the member and an end-effector element sleeve secured to the member and extending from the open end into the housing;

a driver for moving the end-effector element, including a user manipulatable actuator on the base and means including a rod disposed interiorly of the housing coupling the actuator and the end-effector assembly;

an end-effector assembly rotator on the base including:

a user manipulatable rotary actuator; and means for coupling the rotary actuator with the end-effector assembly, the rotary actuator coupling means comprising a rotatable, tubular spindle disposed about the rod and inside the tubular housing;

distal ends of the rod and the spindle extend into and terminat at the end-effector element sleeve;

first and second means operatively connected with the end-effector assembly and the rod and the spindle, respectively, for releasably connecting the rod and the spindle to the end-effector assembly; and release means operable from adjacent the base for engaging and disengaging the first and second means to thereby couple and uncouple the end-effector assembly from the driver and the rotator.

6. A surgical instrument according to claim 5 wherein the first means comprises a transverse locking pin affixed to the distal end of the rod, an axially reciprocable part disposed within the end-effector element sleeve and operatively coupled with the movable end-effector element for translating axial movements of the part into pivotal movements of the movable end-effector element, and a recess formed in the part for axially substantially immovably engaging the locking pin when it is in a first rotational position and for releasing the locking pin when it is in a second rotational position so that, when in the second rotational position, the locking pin can move axially relative to the member.

7. A surgical instrument according to claim 5 wherein the second means comprises first and second, opposing spring arms defining the distal end of the spindle, and a protrusion extending radially inwardly from the end-effector element sleeve into engagement with the spring arms so that rotational movements of the spindle are transmitted to the end-effector element sleeve and therewith to the end-effector elements, and so that a radial inward deflection of the spring arms releases the engagement between the protrusion and the spring arms of the spindle.

8. A surgical instrument according to claim 7 wherein the release means includes means permitting relative axial movements between the housing and the base, and means cooperatively carried by the housing and the spring arms for deflecting the spring arms radially inwardly in response to an axial movement of the housing relative to the base to thereby disengage the protrusion from the spring arms.

9. A surgical instrument according to claim 8 including means for releasably retaining the housing in a position relative to the base in which the protrusion engages the spring arms.

10. A surgical instrument according to claim 9 wherein the releasably retaining means comprises a tubular member nonrotatingly coupled with the base and surrounding the spindle, the spindle and the tubular member defining an annular space shaped to permit axial movement of the housing into the annular space, and a resilient means on the housing positioned to prevent axial movement of the housing into the annular space when in its relaxed position and permitting axial movement of the housing into the annular space when resiliently compressed in a radially inward direction.

11. A surgical instrument according to claim 8 wherein the means for deflecting the spring arms inwardly comprises cooperating, sloping surfaces on an exterior surface of the spring arms and an exterior surface of the housing for translating axial movements of the housing relative to the base into generally radial movements of the spring arms.

12. A surgical instrument according to claim 5 including means nonrotatingly connected to the base for selectively preventing rotational movements of the spindle.

13. A surgical instrument according to claim 5 wherein the driver includes means between the actuator and the rod permitting rotational movement of the rod with the spindle relative to the actuator of the driver.

* * * * *